(12) United States Patent  (10) Patent No.: US 8,022,375 B2
Williams et al.  (45) Date of Patent: Sep. 20, 2011

(54) METHOD AND APPARATUS FOR VALIDATION OF STERILIZATION

(75) Inventors: John A. Williams, Mundelein, IL (US); John A. Martine, Jr., Hendersonville, PA (US)

(73) Assignee: Baxter International Inc., Deerfield, IL (US)

( * ) Notice: Subject to any disclaimer, the term of this patent is extended or adjusted under 35 U.S.C. 154(b) by 40 days.

(21) Appl. No.: 12/642,282

(22) Filed: Dec. 18, 2009

(65) Prior Publication Data

US 2010/0140515 A1   Jun. 10, 2010

Related U.S. Application Data

(62) Division of application No. 10/745,466, filed on Dec. 23, 2003, now Pat. No. 7,641,851.

(51) Int. Cl.
*G01N 21/64* (2006.01)
*G01T 1/02* (2006.01)
*G01N 21/75* (2006.01)
*G01N 23/00* (2006.01)

(52) U.S. Cl. ............. 250/486.1; 250/484.2; 250/484.3; 250/484.5; 250/482.1; 250/455.11; 422/22; 422/400; 422/401; 422/402; 422/403; 422/430; 436/58

(58) Field of Classification Search .............. None
See application file for complete search history.

(56) References Cited

U.S. PATENT DOCUMENTS

| | | |
|---|---|---|
| 3,330,281 A | 7/1967 | Visser |
| 3,330,282 A | 7/1967 | Visser et al. |
| 3,336,924 A | 8/1967 | Sarnoff et al. |
| 3,552,387 A | 1/1971 | Stevens |
| 3,785,481 A | 1/1974 | Allet-Coche |
| 3,788,369 A | 1/1974 | Killinger |
| 3,796,303 A | 3/1974 | Allet-Coche |
| 3,809,225 A | 5/1974 | Allet-Coche |
| 3,826,261 A | 7/1974 | Killinger |
| 3,917,063 A | 11/1975 | Chibret et al. |
| 3,923,059 A | 12/1975 | Ogle |
| 4,014,330 A | 3/1977 | Genese |
| 4,031,895 A | 6/1977 | Porter |
| 4,059,112 A | 11/1977 | Tischlinger |
| 4,116,196 A | 9/1978 | Kaplan et al. |
| 4,170,994 A | 10/1979 | Komatsu |
| 4,210,142 A | 7/1980 | Worder |
| 4,210,173 A | 7/1980 | Choksi et al. |
| 4,226,330 A | 10/1980 | Butler |
| 4,243,080 A | 1/1981 | Choksi et al. |
| 4,247,651 A | 1/1981 | Ohno et al. |

(Continued)

FOREIGN PATENT DOCUMENTS

DE   1766151   4/1968

(Continued)

*Primary Examiner* — Jill Warden
*Assistant Examiner* — Neil N Turk
(74) *Attorney, Agent, or Firm* — K&L Gates LLP

(57) ABSTRACT

An apparatus, system and method for verifying the achievement of a desired sterility assurance level (SAL) for components manipulated within a low-energy electron beam sterilization chamber. The components are preferably pre-sterilized and connected together in an assembly fashion which creates and maintains the sterility of the connection by subjecting the components to low-energy (less than 300 KeV) electron beam radiation. The verification is completed by measuring the sterilization dose delivered to a sensor, also known as a dosimeter, positioned within the sterilization process to simulate the components.

30 Claims, 17 Drawing Sheets

U.S. PATENT DOCUMENTS

| | | |
|---|---|---|
| 4,270,533 A | 6/1981 | Andreas |
| 4,303,071 A | 12/1981 | Smith |
| 4,328,802 A | 5/1982 | Curley et al. |
| 4,346,511 A | 8/1982 | Jones et al. |
| 4,373,526 A | 2/1983 | Kling |
| 4,392,850 A | 7/1983 | Elias et al. |
| 4,392,851 A | 7/1983 | Elias |
| 4,396,383 A | 8/1983 | Hart |
| 4,410,321 A | 10/1983 | Pearson et al. |
| 4,411,358 A | 10/1983 | Bennwik et al. |
| 4,411,662 A | 10/1983 | Pearson |
| 4,424,056 A | 1/1984 | Urquhart et al. |
| 4,424,057 A | 1/1984 | House |
| 4,432,754 A | 2/1984 | Urquhart et al. |
| 4,432,755 A | 2/1984 | Pearson |
| 4,432,756 A | 2/1984 | Urquhart et al. |
| 4,439,182 A | 3/1984 | Huang |
| 4,439,183 A | 3/1984 | Theeuwes |
| 4,458,733 A | 7/1984 | Lyons |
| 4,458,811 A | 7/1984 | Wilkinson |
| 4,465,471 A | 8/1984 | Harris et al. |
| 4,465,488 A | 8/1984 | Richmond et al. |
| 4,465,936 A * | 8/1984 | Ishiguro et al. ............ 250/484.3 |
| 4,467,588 A | 8/1984 | Carveth |
| 4,469,872 A | 9/1984 | Anderson et al. |
| 4,474,574 A | 10/1984 | Wolfe et al. |
| 4,479,793 A | 10/1984 | Urquhart et al. |
| 4,479,794 A | 10/1984 | Urquhart et al. |
| 4,484,909 A | 11/1984 | Urquhart et al. |
| 4,484,920 A | 11/1984 | Kaufman et al. |
| 4,493,703 A | 1/1985 | Butterfield |
| 4,496,646 A | 1/1985 | Ito |
| 4,505,709 A | 3/1985 | Froning et al. |
| 4,507,113 A | 3/1985 | Dunlap |
| 4,507,114 A | 3/1985 | Bohman et al. |
| 4,511,351 A | 4/1985 | Theeuwes |
| 4,511,352 A | 4/1985 | Theeuwes et al. |
| 4,511,353 A | 4/1985 | Theeuwes |
| 4,515,351 A | 5/1985 | Nakayama et al. |
| 4,515,585 A | 5/1985 | Urquhart et al. |
| 4,516,967 A | 5/1985 | Kopfer |
| 4,516,977 A | 5/1985 | Herbert |
| 4,518,386 A | 5/1985 | Tartaglia |
| 4,519,499 A | 5/1985 | Stone et al. |
| 4,521,211 A | 6/1985 | Theeuwes |
| 4,525,162 A | 6/1985 | Urquhart et al. |
| 4,533,348 A | 8/1985 | Wolfe et al. |
| 4,534,757 A | 8/1985 | Geller |
| 4,534,758 A | 8/1985 | Akers et al. |
| 4,538,918 A | 9/1985 | Mittleman |
| 4,539,793 A | 9/1985 | Malek |
| 4,540,089 A | 9/1985 | Maloney |
| 4,540,403 A | 9/1985 | Theeuwes |
| 4,543,094 A | 9/1985 | Barnwell |
| 4,543,101 A | 9/1985 | Crouch |
| 4,548,598 A | 10/1985 | Theeuwes |
| 4,548,599 A | 10/1985 | Urquhart et al. |
| 4,548,606 A | 10/1985 | Larkin |
| 4,550,825 A | 11/1985 | Sutryn et al. |
| 4,552,277 A | 11/1985 | Richardson et al. |
| 4,552,555 A | 11/1985 | Theeuwes |
| 4,552,556 A | 11/1985 | Urquhart et al. |
| 4,561,110 A | 12/1985 | Herbert |
| 4,564,054 A | 1/1986 | Gustavsson |
| 4,568,331 A | 2/1986 | Fischer et al. |
| 4,568,336 A | 2/1986 | Cooper |
| 4,568,346 A | 2/1986 | van Dijk |
| 4,573,967 A | 3/1986 | Hargrove et al. |
| 4,573,993 A | 3/1986 | Hoag et al. |
| 4,576,211 A | 3/1986 | Valentini et al. |
| 4,579,553 A | 4/1986 | Urquhart et al. |
| 4,581,016 A | 4/1986 | Gettig |
| 4,583,971 A | 4/1986 | Bocquet et al. |
| 4,583,981 A | 4/1986 | Urquhart et al. |
| 4,586,922 A | 5/1986 | Theeuwes |
| 4,589,867 A | 5/1986 | Israel |
| 4,589,879 A | 5/1986 | Pearson |
| 4,590,234 A | 5/1986 | Tasaka et al. |
| 4,596,555 A | 6/1986 | Theeuwes |
| 4,601,704 A | 7/1986 | Larkin |
| 4,602,910 A | 7/1986 | Larkin |
| 4,606,734 A | 8/1986 | Larkin et al. |
| 4,607,671 A | 8/1986 | Aalto et al. |
| 4,608,043 A | 8/1986 | Larkin |
| 4,610,684 A | 9/1986 | Knox et al. |
| 4,613,326 A | 9/1986 | Szwarc |
| 4,614,267 A | 9/1986 | Larkin |
| 4,614,515 A | 9/1986 | Tripp et al. |
| 4,623,334 A | 11/1986 | Riddell |
| 4,629,080 A | 12/1986 | Carveth |
| 4,630,727 A | 12/1986 | Feriani et al. |
| 4,632,244 A | 12/1986 | Landau |
| 4,637,934 A | 1/1987 | White |
| 4,650,475 A | 3/1987 | Smith et al. |
| 4,652,763 A | 3/1987 | Nablo |
| 4,662,878 A | 5/1987 | Lindmayer |
| 4,664,650 A | 5/1987 | Urquhart et al. |
| 4,668,219 A | 5/1987 | Israel |
| 4,673,404 A | 6/1987 | Gustavsson |
| 4,675,020 A | 6/1987 | McPhee |
| 4,692,144 A | 9/1987 | Carpenter |
| 4,693,706 A | 9/1987 | Ennis, III |
| 4,695,272 A | 9/1987 | Berglund et al. |
| 4,703,864 A | 11/1987 | Larkin et al. |
| 4,704,535 A | 11/1987 | Leber et al. |
| 4,715,854 A | 12/1987 | Vaillancourt |
| 4,717,388 A | 1/1988 | Steer et al. |
| 4,722,733 A | 2/1988 | Howson |
| 4,723,956 A | 2/1988 | Schnell et al. |
| 4,727,985 A | 3/1988 | McNeirney et al. |
| 4,731,053 A | 3/1988 | Hoffman |
| 4,735,608 A | 4/1988 | Sardam |
| 4,740,103 A | 4/1988 | Theeuwes |
| 4,740,197 A | 4/1988 | Theeuwes |
| 4,740,198 A | 4/1988 | Theeuwes |
| 4,740,199 A | 4/1988 | Theeuwes |
| 4,740,200 A | 4/1988 | Theeuwes |
| 4,740,201 A | 4/1988 | Theeuwes |
| 4,741,734 A | 5/1988 | Theeuwes |
| 4,741,735 A | 5/1988 | Theeuwes |
| 4,743,229 A | 5/1988 | Chu |
| 4,747,834 A | 5/1988 | Prindle |
| 4,752,292 A | 6/1988 | Lopez et al. |
| 4,757,911 A | 7/1988 | Larkin et al. |
| 4,759,756 A | 7/1988 | Forman et al. |
| 4,778,453 A | 10/1988 | Lopez |
| 4,781,679 A | 11/1988 | Larkin |
| 4,782,841 A | 11/1988 | Lopez |
| 4,784,259 A | 11/1988 | Grabenkort |
| 4,784,658 A | 11/1988 | Grabenkort |
| 4,785,858 A | 11/1988 | Valentini et al. |
| 4,786,279 A | 11/1988 | Wilkinson et al. |
| 4,787,429 A | 11/1988 | Valentini et al. |
| 4,790,820 A | 12/1988 | Theeuwes |
| 4,804,360 A | 2/1989 | Kamen |
| 4,804,366 A | 2/1989 | Zdeb et al. |
| 4,808,381 A | 2/1989 | McGregor et al. |
| 4,816,024 A | 3/1989 | Sitar et al. |
| 4,819,659 A | 4/1989 | Sitar |
| 4,820,269 A | 4/1989 | Riddell |
| 4,822,351 A | 4/1989 | Purcell |
| 4,832,690 A | 5/1989 | Kuu |
| 4,834,149 A | 5/1989 | Fournier et al. |
| 4,834,152 A | 5/1989 | Howson et al. |
| 4,842,028 A | 6/1989 | Kaufman et al. |
| 4,850,978 A | 7/1989 | Dudar et al. |
| 4,857,052 A | 8/1989 | Theeuwes |
| 4,861,335 A | 8/1989 | Reynolds |
| 4,861,585 A | 8/1989 | Galef, Jr. et al. |
| 4,865,354 A | 9/1989 | Allen |
| 4,871,354 A | 10/1989 | Conn et al. |
| 4,871,360 A | 10/1989 | Theeuwes |
| 4,871,463 A | 10/1989 | Taylor et al. |
| 4,872,494 A | 10/1989 | Coccia |
| 4,874,366 A | 10/1989 | Zdeb et al. |
| 4,874,368 A | 10/1989 | Miller et al. |
| 4,883,483 A | 11/1989 | Lindmayer |

| | | | | | |
|---|---|---|---|---|---|
| 4,886,495 A | 12/1989 | Reynolds | 5,186,323 A | 2/1993 | Pfleger |
| 4,898,209 A | 2/1990 | Zbed | 5,188,615 A | 2/1993 | Haber et al. |
| 4,906,103 A | 3/1990 | Kao | 5,188,629 A | 2/1993 | Shimoda |
| 4,908,019 A | 3/1990 | Urquhart et al. | 5,195,658 A | 3/1993 | Hoshino |
| 4,909,290 A | 3/1990 | Coccia | 5,195,986 A | 3/1993 | Kamen |
| 4,911,708 A | 3/1990 | Maezaki et al. | 5,196,001 A | 3/1993 | Kao |
| 4,915,689 A | 4/1990 | Theeuwes | 5,199,947 A | 4/1993 | Lopez et al. |
| 4,927,013 A | 5/1990 | Van Brunt et al. | 5,199,948 A | 4/1993 | McPhee |
| 4,927,423 A | 5/1990 | Malmborg | 5,200,200 A | 4/1993 | Veech |
| 4,927,605 A | 5/1990 | Dorn et al. | 5,201,705 A | 4/1993 | Berglund et al. |
| 4,931,048 A | 6/1990 | Lopez | 5,207,509 A | 5/1993 | Herbert |
| 4,936,445 A | 6/1990 | Grabenkort | 5,209,201 A | 5/1993 | Horie et al. |
| 4,936,829 A | 6/1990 | Zdeb et al. | 5,209,347 A | 5/1993 | Fabisiewicz et al. |
| 4,936,841 A | 6/1990 | Aoki et al. | 5,211,201 A | 5/1993 | Kamen et al. |
| 4,944,736 A | 7/1990 | Holtz | 5,211,285 A | 5/1993 | Haber et al. |
| 4,948,000 A | 8/1990 | Grabenkort | 5,222,946 A | 6/1993 | Kamen |
| 4,950,237 A | 8/1990 | Henault et al. | 5,226,878 A | 7/1993 | Young |
| 4,961,495 A | 10/1990 | Yoshida et al. | 5,226,900 A | 7/1993 | Bancsi et al. |
| 4,968,299 A | 11/1990 | Ahlstrand et al. | RE34,365 E | 8/1993 | Theeuwes |
| 4,969,883 A | 11/1990 | Gilbert et al. | 5,232,029 A | 8/1993 | Knox et al. |
| 4,973,307 A | 11/1990 | Theeuwes | 5,232,109 A | 8/1993 | Tirrell et al. |
| 4,975,589 A * | 12/1990 | Chamberlain et al. ..... 250/484.3 | 5,246,142 A | 9/1993 | DiPalma et al. |
| 4,978,337 A | 12/1990 | Theeuwes | 5,247,972 A | 9/1993 | Tetreault |
| 4,979,942 A | 12/1990 | Wolf et al. | 5,250,028 A | 10/1993 | Theeuwes et al. |
| 4,982,875 A | 1/1991 | Pozzi et al. | 5,257,985 A | 11/1993 | Puhl |
| 4,983,164 A | 1/1991 | Hook et al. | 5,257,986 A | 11/1993 | Herbert et al. |
| 4,985,016 A | 1/1991 | Theeuwes et al. | 5,257,987 A | 11/1993 | Athayde et al. |
| 4,986,322 A | 1/1991 | Chibret et al. | 5,259,843 A | 11/1993 | Watanabe et al. |
| 4,994,031 A | 2/1991 | Theeuwes | 5,259,954 A | 11/1993 | Taylor |
| 4,994,056 A | 2/1991 | Ikeda | 5,261,902 A | 11/1993 | Okada et al. |
| 4,996,579 A | 2/1991 | Chu | 5,267,646 A | 12/1993 | Inoue et al. |
| 4,997,083 A | 3/1991 | Loretti et al. | 5,267,957 A | 12/1993 | Kriesel et al. |
| 4,997,430 A | 3/1991 | Van der Heiden et al. | 5,279,576 A | 1/1994 | Loo et al. |
| 5,002,530 A | 3/1991 | Recker et al. | 5,279,579 A | 1/1994 | D'Amico |
| 5,023,119 A | 6/1991 | Yamakoshi | 5,279,583 A | 1/1994 | Shober, Jr. et al. |
| 5,024,657 A | 6/1991 | Needham et al. | 5,281,198 A | 1/1994 | Haber et al. |
| 5,030,203 A | 7/1991 | Wolf, Jr. et al. | 5,281,206 A | 1/1994 | Lopez |
| 5,032,117 A | 7/1991 | Motta | 5,286,257 A | 2/1994 | Fischer |
| 5,045,081 A | 9/1991 | Dysarz | 5,287,961 A | 2/1994 | Herran |
| 5,049,129 A | 9/1991 | Zdeb et al. | 5,289,585 A | 2/1994 | Kock et al. |
| 5,049,135 A | 9/1991 | Davis | 5,289,858 A | 3/1994 | Grabenkort |
| 5,049,754 A | 9/1991 | Hoelscher et al. | 5,302,603 A | 4/1994 | Crawley et al. |
| 5,061,264 A | 10/1991 | Scarrow | 5,303,751 A | 4/1994 | Slater et al. |
| 5,064,059 A | 11/1991 | Ziegler et al. | 5,304,130 A | 4/1994 | Button et al. |
| 5,069,671 A | 12/1991 | Theeuwes | 5,304,163 A | 4/1994 | Bonnici et al. |
| 5,074,844 A | 12/1991 | Zdeb et al. | 5,304,165 A | 4/1994 | Haber et al. |
| 5,074,849 A | 12/1991 | Sachse | 5,306,242 A | 4/1994 | Joyce et al. |
| D323,389 S | 1/1992 | Aoki et al. | 5,308,287 A | 5/1994 | Gunsing |
| 5,080,652 A | 1/1992 | Sancoff et al. | 5,308,347 A | 5/1994 | Sunago et al. |
| 5,083,031 A | 1/1992 | Hoelscher et al. | 5,320,603 A | 6/1994 | Vetter et al. |
| 5,084,040 A | 1/1992 | Sutter | 5,328,464 A | 7/1994 | Kriesel et al. |
| 5,088,996 A | 2/1992 | Kopfer et al. | 5,330,048 A | 7/1994 | Haber et al. |
| 5,100,394 A | 3/1992 | Dudar et al. | 5,330,426 A | 7/1994 | Kriesel et al. |
| 5,102,408 A | 4/1992 | Hamacher | 5,330,450 A | 7/1994 | Lopez |
| 5,104,375 A | 4/1992 | Wolf et al. | 5,330,462 A | 7/1994 | Nakamura |
| 5,114,004 A | 5/1992 | Isono et al. | 5,330,464 A | 7/1994 | Mathias et al. |
| 5,114,411 A | 5/1992 | Haber et al. | 5,332,399 A | 7/1994 | Grabenkort et al. |
| 5,116,315 A | 5/1992 | Capozzi et al. | 5,334,178 A | 8/1994 | Haber et al. |
| 5,116,316 A | 5/1992 | Sertic et al. | 5,334,180 A | 8/1994 | Adolf et al. |
| 5,117,875 A | 6/1992 | Marrucchi | 5,334,188 A | 8/1994 | Inoue et al. |
| 5,122,123 A | 6/1992 | Vaillancourt | 5,335,773 A | 8/1994 | Haber et al. |
| 5,125,892 A | 6/1992 | Drudik | 5,336,180 A | 8/1994 | Kriesel et al. |
| 5,125,908 A | 6/1992 | Cohen | 5,342,346 A | 8/1994 | Honda et al. |
| 5,126,175 A | 6/1992 | Yamakoshi | 5,342,347 A | 8/1994 | Kikuchi et al. |
| 5,129,894 A | 7/1992 | Sommermeyer et al. | 5,344,414 A | 9/1994 | Lopez et al. |
| 5,137,511 A | 8/1992 | Reynolds | 5,348,060 A | 9/1994 | Futagawa et al. |
| 5,147,324 A | 9/1992 | Skakoon et al. | 5,348,600 A | 9/1994 | Ishii |
| 5,152,965 A | 10/1992 | Fisk et al. | 5,350,372 A | 9/1994 | Ikeda et al. |
| 5,156,598 A | 10/1992 | Skakoon et al. | 5,350,546 A | 9/1994 | Takeuchi et al. |
| 5,158,546 A | 10/1992 | Haber et al. | 5,352,191 A | 10/1994 | Sunago et al. |
| 5,160,320 A | 11/1992 | Yum et al. | 5,352,196 A | 10/1994 | Haber et al. |
| 5,167,642 A | 12/1992 | Fowles | 5,352,210 A | 10/1994 | Marrucchi |
| 5,169,388 A | 12/1992 | McPhee | 5,353,961 A | 10/1994 | Debush |
| 5,171,214 A | 12/1992 | Kolber et al. | 5,356,380 A | 10/1994 | Hoekwater et al. |
| 5,171,219 A | 12/1992 | Fujioka et al. | 5,358,501 A | 10/1994 | Meyer |
| 5,171,220 A | 12/1992 | Morimoto | 5,360,410 A | 11/1994 | Wacks |
| 5,176,634 A | 1/1993 | Smith et al. | 5,364,350 A | 11/1994 | Dittmann |
| 5,176,673 A | 1/1993 | Marrucchi | 5,364,369 A | 11/1994 | Reynolds |
| 5,181,909 A | 1/1993 | McFarlane | 5,364,371 A | 11/1994 | Kamen |

| | | | | | | |
|---|---|---|---|---|---|---|
| 5,364,384 | A | 11/1994 | Grabenkort et al. | 5,554,128 | A | 9/1996 | Hedges |
| 5,368,586 | A | 11/1994 | Van Der Heiden et al. | 5,560,403 | A | 10/1996 | Balteau et al. |
| 5,370,164 | A | 12/1994 | Galloway | 5,566,729 | A | 10/1996 | Grabenkort et al. |
| 5,373,966 | A | 12/1994 | O'Reilly et al. | 5,569,191 | A | 10/1996 | Meyer |
| 5,374,264 | A | 12/1994 | Wadsworth, Jr. | 5,569,192 | A | 10/1996 | van der Wal |
| 5,376,079 | A | 12/1994 | Holm | 5,569,193 | A | 10/1996 | Hofstetter et al. |
| 5,380,281 | A | 1/1995 | Tomellini et al. | 5,573,527 | A | 11/1996 | Macabasco et al. |
| 5,380,287 | A | 1/1995 | Kikuchi et al. | 5,575,310 | A | 11/1996 | Kamen et al. |
| 5,380,315 | A | 1/1995 | Isono et al. | 5,577,369 | A | 11/1996 | Becker et al. |
| 5,385,545 | A | 1/1995 | Kriesel et al. | 5,584,808 | A | 12/1996 | Healy |
| 5,385,546 | A | 1/1995 | Kriesel et al. | 5,593,028 | A | 1/1997 | Haber et al. |
| 5,385,547 | A | 1/1995 | Wong et al. | 5,595,314 | A | 1/1997 | Weiler |
| 5,386,372 | A | 1/1995 | Kobayashi et al. | 5,596,193 | A | 1/1997 | Chutjian et al. |
| 5,393,497 | A | 2/1995 | Haber et al. | 5,603,695 | A | 2/1997 | Erickson |
| 5,397,303 | A | 3/1995 | Sancoff et al. | 5,603,696 | A | 2/1997 | Williams et al. |
| 5,398,851 | A | 3/1995 | Sancoff et al. | 5,605,542 | A | 2/1997 | Tanaka et al. |
| 5,401,253 | A | 3/1995 | Reynolds | 5,611,792 | A | 3/1997 | Gustafsson |
| 5,409,141 | A | 4/1995 | Kikuchi et al. | 5,620,434 | A | 4/1997 | Brony |
| 5,418,167 | A | 5/1995 | Matner et al. | 5,624,405 | A | 4/1997 | Futagawa et al. |
| 5,423,421 | A | 6/1995 | Inoue et al. | 5,641,010 | A | 6/1997 | Maier |
| 5,423,753 | A | 6/1995 | Fowles et al. | 5,661,305 | A | 8/1997 | Lawrence et al. |
| 5,423,793 | A | 6/1995 | Isono et al. | 5,669,891 | A | 9/1997 | Vaillancourt |
| 5,423,796 | A | 6/1995 | Shikhman et al. | 5,688,254 | A | 11/1997 | Lopez et al. |
| 5,425,447 | A | 6/1995 | Farina | 5,709,666 | A | 1/1998 | Reynolds |
| 5,425,528 | A | 6/1995 | Rains et al. | 5,743,312 | A | 4/1998 | Pfeifer et al. |
| 5,429,256 | A | 7/1995 | Kestenbaum | 5,827,262 | A | 10/1998 | Neftel et al. |
| 5,429,603 | A | 7/1995 | Morris | 5,897,526 | A | 4/1999 | Vaillancourt |
| 5,429,614 | A | 7/1995 | Fowles et al. | 5,989,237 | A | 11/1999 | Fowles et al. |
| 5,435,076 | A | 7/1995 | Hjertman et al. | 6,019,750 | A | 2/2000 | Fowles et al. |
| 5,445,631 | A | 8/1995 | Uchida | 6,022,339 | A | 2/2000 | Fowles et al. |
| 5,456,678 | A | 10/1995 | Nicoletti | 6,063,068 | A | 5/2000 | Fowles et al. |
| 5,458,593 | A | 10/1995 | Macabasco et al. | 6,071,270 | A | 6/2000 | Fowles et al. |
| 5,462,526 | A | 10/1995 | Barney et al. | 6,090,092 | A | 7/2000 | Fowles et al. |
| 5,464,123 | A | 11/1995 | Scarrow | 6,140,657 | A | 10/2000 | Wakalopulos et al. |
| 5,467,337 | A | 11/1995 | Matsumoto | 6,232,610 | B1 | 5/2001 | Pageau et al. |
| 5,470,327 | A | 11/1995 | Helgren et al. | 6,378,714 | B1 | 4/2002 | Jansen et al. |
| 5,472,022 | A | 12/1995 | Michel et al. | 6,610,040 | B1 | 8/2003 | Fowles et al. |
| 5,472,422 | A | 12/1995 | Ljungquist | 2003/0071229 | A1 | 4/2003 | Ishidoya et al. |
| 5,474,540 | A | 12/1995 | Miller et al. | 2003/0194344 | A1 | 10/2003 | Brafford et al. |
| 5,478,337 | A | 12/1995 | Okamoto et al. | | | | |
| 5,484,406 | A | 1/1996 | Wong et al. | | | | |
| 5,484,410 | A | 1/1996 | Kriesel et al. | | | | |

FOREIGN PATENT DOCUMENTS

| | | |
|---|---|---|
| DE | 1913926 | 3/1969 |
| EP | 0 091 310 A2 | 4/1983 |
| EP | 0 285 424 A1 | 3/1988 |
| EP | 0 335 378 A2 | 4/1989 |
| EP | 0 363 770 A1 | 4/1990 |
| EP | 0 395 758 A1 | 7/1990 |
| EP | 0 499 764 A1 | 8/1992 |
| EP | 0 692 235 A1 | 1/1996 |
| GB | 2 211 104 A | 10/1987 |
| JP | 4156849 A2 | 10/1990 |
| JP | 7255820 A2 | 3/1994 |
| JP | 8238300 A2 | 3/1995 |
| JP | WO 97/25015 | 7/1997 |
| JP | 09-276370 | 10/1997 |
| JP | 10024089 A2 | 1/1998 |
| WO | WO 83/03540 | 10/1983 |
| WO | WO 85/03432 | 1/1985 |
| WO | WO 90/03536 | 9/1989 |
| WO | WO 92/11897 | 7/1992 |
| WO | WO 93/02723 | 2/1993 |
| WO | WO 93/09825 | 5/1993 |
| WO | WO 99/39751 | 8/1999 |

| | | | |
|---|---|---|---|
| 5,489,266 | A | 2/1996 | Grimard |
| 5,490,848 | A | 2/1996 | Finley et al. |
| 5,492,147 | A | 2/1996 | Challender et al. |
| 5,492,219 | A | 2/1996 | Stupar |
| 5,493,774 | A | 2/1996 | Grabenkort |
| 5,494,190 | A | 2/1996 | Boettcher |
| 5,496,302 | A | 3/1996 | Minshall et al. |
| 5,501,887 | A | 3/1996 | Tanaka et al. |
| 5,509,898 | A | 4/1996 | Isono et al. |
| 5,510,115 | A | 4/1996 | Breillatt, Jr. et al. |
| 5,514,090 | A | 5/1996 | Kriesel et al. |
| 5,520,972 | A | 5/1996 | Ezaki et al. |
| 5,522,804 | A | 6/1996 | Lynn |
| 5,526,853 | A | 6/1996 | McPhee et al. |
| 5,531,683 | A | 7/1996 | Kriesel et al. |
| 5,533,389 | A | 7/1996 | Kamen et al. |
| 5,533,973 | A | 7/1996 | Piontek et al. |
| 5,533,994 | A | 7/1996 | Meyer |
| 5,535,746 | A | 7/1996 | Hoover et al. |
| 5,536,469 | A | 7/1996 | Jonsson et al. |
| 5,538,506 | A | 7/1996 | Farris et al. |
| 5,540,674 | A | 7/1996 | Karas et al. |
| 5,547,471 | A | 8/1996 | Thompson et al. |
| 5,554,125 | A | 9/1996 | Reynolds |

* cited by examiner

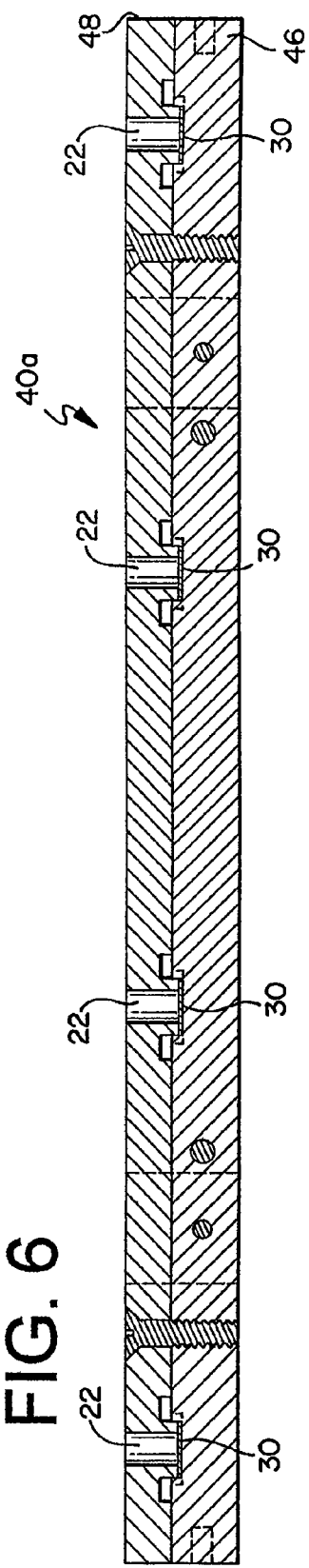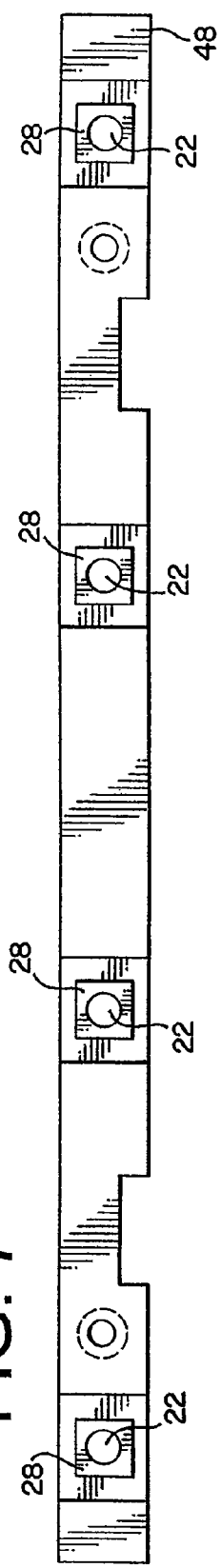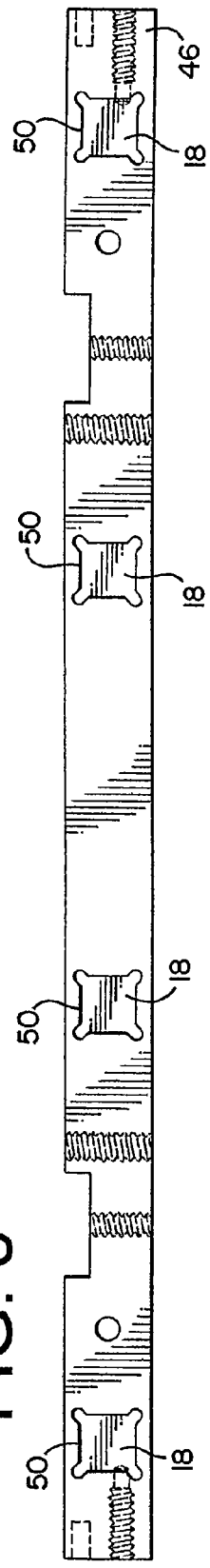

METHOD AND APPARATUS FOR VALIDATION OF STERILIZATION

PRIORITY CLAIM

This application is a divisional application of and claims the benefit of and priority to U.S. application of patent application Ser. No. 10/745,466 filed Dec. 23, 2003, the entire contents of which are expressly incorporated herein by reference.

TECHNICAL FIELD OF INVENTION

The present invention relates generally to the field of automated inspection, staging, and assembly of pre-sterilized components, specifically medical components, to maintain sterility via a low-energy electron beam field.

BACKGROUND

In general, the sterilization of medical products depends upon the ability of the process to kill pathogenic microorganisms. The application of radiation to sterilize medical products is widely used throughout the world and recognized as a safe, effective form of sterilization. The first commercial application of electron beam sterilization processing for medical devices was developed by Ethicon Inc., a subsidiary of Johnson and Johnson in 1956. In the early 1960s the use of gamma rays from Cobalt-60 for the sterilization of disposable medical devices was being developed in the United Kingdom. Because of the poor reliability of the early electron beam systems, the radiation sterilization of medical products was dominated by Cobalt-60 (gamma) irradiators, which had no similar reliability issues.

With the advent of national laboratories devoted to high-energy physics research, a major effort was put into improving the reliability and performance of critical accelerator components. By the 1970s, industry's involvement in developing radiographic and oncology machines further enhanced the durability and reliability of electron accelerators. This improvement of component performance—along with the integration of computerized controls—encouraged reevaluation of the commercial possibilities of the technology. Soon thereafter, interest in high-energy (>300 keV) E-beam based sterilization was rapidly growing.

Perhaps the largest industrial application of radiation is the modification of polymers. Radiation is used to polymerize and cure monomers into polymers, to cross-link polymers, and to graft different types of monomers onto polymer molecules to form new materials with special properties. Radiation is also used for the intentional degradation of polymers and for tailoring of molecular weight distributions to serve special industrial and commercial purposes. This industrial application of radiation is dominated by low energy (<300 keV) electron beam systems.

In 1999, use of a low-energy (<300 KeV) E-beam system in sterilization of medical devices was described in U.S. patent application Ser. No. 09/294,964, filed Apr. 20, 1999, now U.S. Pat. No. 7,264,771, assigned to the assignee of the present application, Baxter International, the relevant disclosure of which is hereby incorporated by reference. E-beam sterilization unit size and cost were two big factors feeding the move toward low-energy sterilization systems. Depth of the sterilizing radiation penetration became the tradeoff. Where high-energy systems may achieve penetration depths of over a meter, low-energy beams are limited to penetration depths of as low as only a few microns.

The significantly reduced radiation penetration of low-energy electron beams used for medical device sterilization raised the issue of sterility validation as a processing concern. The FDA requires that "all processes used to produce medical devices be validated" (21 C.F.R. §820.752), including E-beam sterilization. The goal of such validation is to determine the minimum exposure dose that can be used to meet a desired sterility assurance level and allow "dosimetric release," which is the determination that a product is sterile based on physical irradiation process data rather than actual sterility testing.

Therefore, validation must begin with the selection of a sterility assurance level (SAL), a measure of the probability that one unit in a batch will remain non-sterile after being exposed to a specific sterilant. For example, an SAL of 10-3 means that one device in a thousand may be non-sterile. Selecting the proper SAL occurs during a dose-setting phase of radiation sterilization validation. In many cases, the intended use of the device will dictate the need for a particular SAL. The commonly accepted SAL for invasive medical devices is 10-6. However, some European countries only recognize 10-6 SAL for a claim of "sterile." In such cases, the country of intended use will dictate the SAL as much as the device's intended use.

Although both gamma and ethylene oxide-gas sterilization are validated, effective and readily available technologies, the increased focus on E-beam can be ascribed to its having the shortest process cycle of any currently recognized sterilization method. In both high- and low-energy E-beam processing, the products are scanned for seconds, with the bulk of the processing time devoted to transporting the products into and out of a shielded booth. With the use of established and recognized dosimetric release procedures, a product under going high-energy E-beam sterilization can be released from quarantine as sterile within 30 minutes. The prior art, however, has not sufficiently developed a method for validation and routine monitoring of low-energy E-beam sterilization.

As a solution to this problem, the present invention has been developed which provides an apparatus for use in the validation of low-energy electron beam sterilization systems. Furthermore, the invention provides a method that cost-effectively and reliably provides for the routine dosimetric monitoring of the sterilization process for low-energy electron beam sterilization systems.

SUMMARY

Generally, the present invention comprises a method and apparatus for verifying the radiation dose delivered to achieve the sterilization of components, such as medical devices, in a low-energy electron beam sterilization system.

Specifically, as one embodiment of the present invention, a single-site dosimeter assembly is disclosed. The assembly is comprised of a first component block having a cavity, suitable for positioning a dosimeter therein, and a coaxially configured passage to allow for the travel of radiation into the cavity portion. A second component block affixes to the first block and comprises an interior surface with a protrusion configured to abut an interior surface of the cavity, thereby retaining the dosimeter therein. The assembly may further comprise a mechanism to affix the first dosimeter block to the second dosimeter block, and affix the resulting assembly to a radiation sterilization site.

A method for verifying sterilization of components in a low-energy electron-beam sterilization system is also described. The novel method comprises the steps of placing a component within a low-energy electron-beam sterilization system as a site to be sterilized, designating an indicator site within the sterilization system as a site to be used to indicate achievement of a dose level, determining a sterilization dose level which when achieved results in a desired sterility assurance level (SAL) of a component, establishing a correlation between a dose achieved at the indicator site and a dose achieved at the sterilization site, exposing the designated sites to a sterilizing source to achieve a sterilization dose at the sterilization site and a correlated dose at the indicator site, determining the dose achieved at the indicator site, and ascertaining the efficacy of the sterilization dose achieved at the sterilization site based on the determined dose at the correlated indicator site.

In one embodiment of the disclosed method, the step of establishing a correlation comprises the steps of exposing the designated sites to a sterilizing source to mimic operation of a sterilization system, measuring the sterilizing dose received at each site, and repeating exposing and measuring steps to determine a relationship between the sterilizing dose level measured at a sterilizing site and a sterilizing dose level measured at an indication site.

An assembly capable of verifying sterilization of two components to be connected together is also disclosed. The assembly comprises a first component carriage and a second component carriage. Each carriage preferably comprises a component site requiring a threshold sterilization dose to achieve sterility of a component, and a dosimeter site positioned approximate the component site and having a dosimeter to receive an applied dose which corresponds to a sterilization dose level received by the component site.

It is important to note that the dose ultimately achieved at the indicator site is not necessarily equal to that achieved at the sterilization site, nor is it necessary that the dose at the indicator site even be a sterilizing dose.

In an embodiment of the assembly, the first component carriage further comprises a mechanism to control the sterilization dose received by the dosimeter at the dosimeter site. The mechanism in one embodiment comprises a passage having a diameter and a depth, with the passage being positioned above the dosimeter site. The diameter and depth of the passage may be of any suitable sizes to allow for the proper amount of radiation exposure.

The assembled dosimeter site preferably comprises a first holder block having a receptacle defined within a wall of the holder block to contain a dosimeter therein, and an passage, having a diameter and depth, through the wall within the periphery of the receptacle, and a second holder block configured with a mating section which fits within the receptacle of the first holder block to abut the dosimeter therein.

The first component carriage may comprise from 1 to 10 component sites and from 1 to 15 dosimeter sites.

These and other features are provided in the present invention. A more detailed description of the several components, their purposes, and possible alternative embodiments are set forth in the detailed discussion following.

Additional features and advantages are described herein, and will be apparent from the following Detailed Description and the figures.

BRIEF DESCRIPTION OF THE FIGURES

The details of the present invention can be more readily understood when the following description is considered in combination with the appended drawings where:

FIG. 6 is a cross-sectional view of the assembled embodiment of the dosimeter holder shown in FIG. 5;

FIG. 7 is a plan view of the second or upper block of the embodiment shown in FIG. 6;

FIG. 8 is a plan view of the first or lower block of the embodiment shown in FIG. 6;

DETAILED DESCRIPTION

Figure 1:
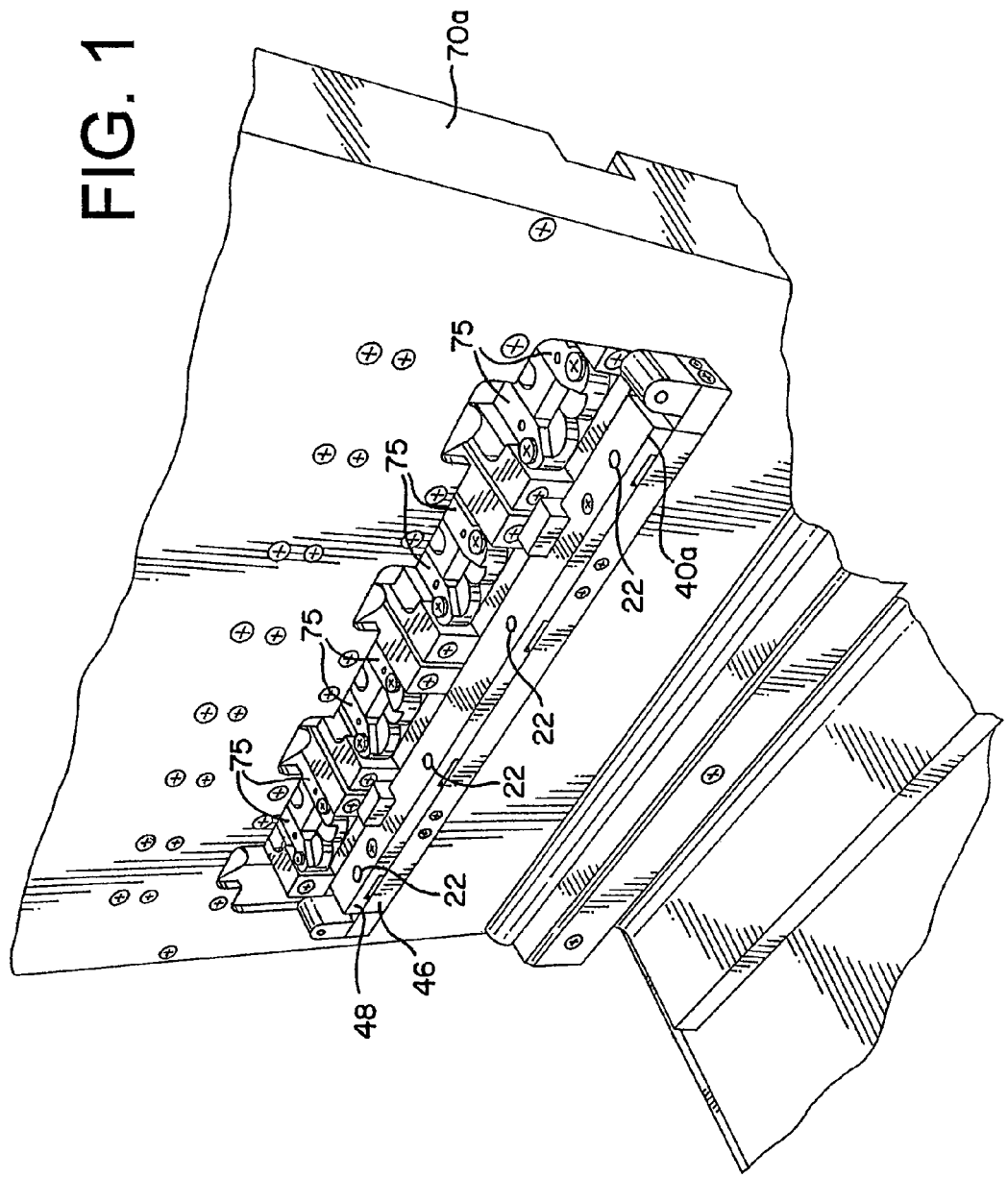
FIG. 1 is a perspective view of the backside of a bag sterilization pallet having attached thereto one embodiment of the present dosimeter holder of the present invention.
Figure 2:
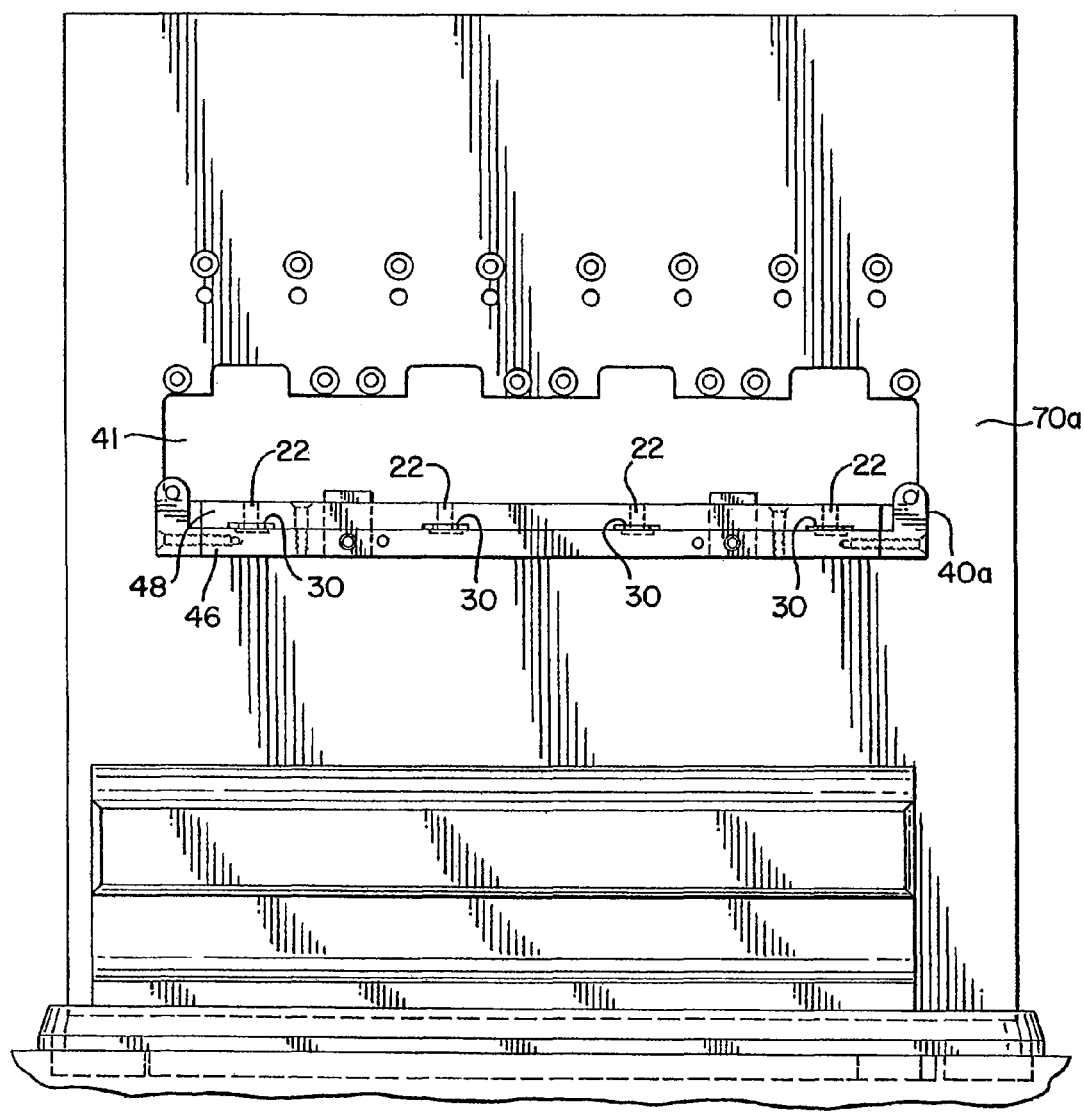
FIG. 2 is a back elevation view showing an embodiment of the present invention attached to the bag sterilization pallet of FIG. 1.

While the present invention is susceptible of embodiment in many different forms, this disclosure will describe in detail at least one preferred embodiment, and possible alternative embodiments, of the invention with the understanding that the present disclosure is to be considered merely as an exemplification of the principles of the invention and is not intended to limit the broad aspect of the invention to the specific embodiments illustrated.

The present invention provides an assembly for verification of low-energy e-beam sterilization, as well as methods of using the same. For purposes of the present application, the following definitions of terms are used:

Sterility (Sterilize, Sterilization, etc.,), the act of using or condition achieved after use of a physical or chemical procedure to destroy microbial life, including pathogens such as highly resistant bacterial endospores and viruses;

Sterility assurance level (SAL), a measure of the probability that one unit in a batch will remain non-sterile after being exposed to a specific sterilant;

Low-Energy Electron-Beam, an electron beam or beam array which operates at an energy of less than 300 KeV, more preferably in the range of from about 60 to about 150 KeV;

Validation of Sterilization, a process for determining that exposure to a specific dose or level of radiation will result in a desired sterility assurance level (SAL);

Verification of Sterility, a process for determining that a desired component was exposed to the proper amount of radiation to achieve sterility;

Dosimeter, any device that, when irradiated, exhibits a quantifiable change in some property of the device that can be related to absorbed dose in a given material using appropriate analytical instrumentation and techniques;

Component, any medical device capable of being sterilized, such as, for example, drug vial, syringe, reconstitution device, medical tubing, IV bag, cannula, and the like; and Pallet (or Carriage), a device configured for the housing, transport, and, in some cases, shielding of components in a sterilization process, particularly a sterile connection process.

The prior art discloses methods and apparatus for the verification of ultraviolet sterilization (U.S. Pat. No. 6,475,433 to McGeorge et al.) and the linal sterilization (U.S. Pat. No. 6,340,590 to Gillis). Verification of sterilization in a low-energy electron beam system, however, provides far different challenges to those skilled in the art, as the following specification will address.

Accordingly, the present invention involves methods and apparatus for automatically verifying sterilization of components, particularly where two or more components are to be connected in a sterile field. While the components may be made from any known material, preferably the objects are made from a readily sterilizable material. For example, a glass drug vial may be sterilely connected to a rigid plastic reconstitution device to form a vial/device assembly (VDA). The assembly may then be sterile-connected to a flexible tubing portion of a fluid bag to form a final assembly. Such a vial/device assembly (VDA) and final assembly are shown in the appended drawings and described herein. However, the claimed invention should not be limited to these embodiments, which are included for exemplary purposes only.

After being pre-sterilized, the components are received into a sterilization pallet utilizing the present invention for verification. Sterilization pallets are used to house, transport, and, in some cases, shield portions of the components as they move within a sterilization system. Such pallets may be specifically designed for containing a single-sized component, such as a reconstitution device, or may be adjustable for varying sizes of a component, such as drug vials. Referring generally to FIGS. 1-18, some example sterilization pallets can be seen.

FIGS. 1-4 illustrate a bag pallet 70a. FIGS. 9-12 illustrate a vial and device pallet 70b. The bag pallet 70a is preferably a metal structure which functions to maintain at least one bag component in position for connection to at least one other component while at least a portion of those components are maintained within an electron beam field. Likewise, the vial and device pallet 70b is preferably a substantially metal structure that also functions to position components for connection while being maintained within an electron beam field. In the case of both pallets, it is also a function to shield portions of the components from the electron beam field during connection. As those skilled in the art would understand, the physical form of the pallets depends on many factors, including, for example, the dimensions of the components being connected, the connection strategy, etc. A further description of these pallet devices is more fully set forth in co-pending U.S. patent application Ser. No. 10/744,496, filed Dec. 23, 2003, and assigned to the assignee of the present invention, Baxter International, the relevant disclosure of which is hereby incorporated by reference.

Figure 3:
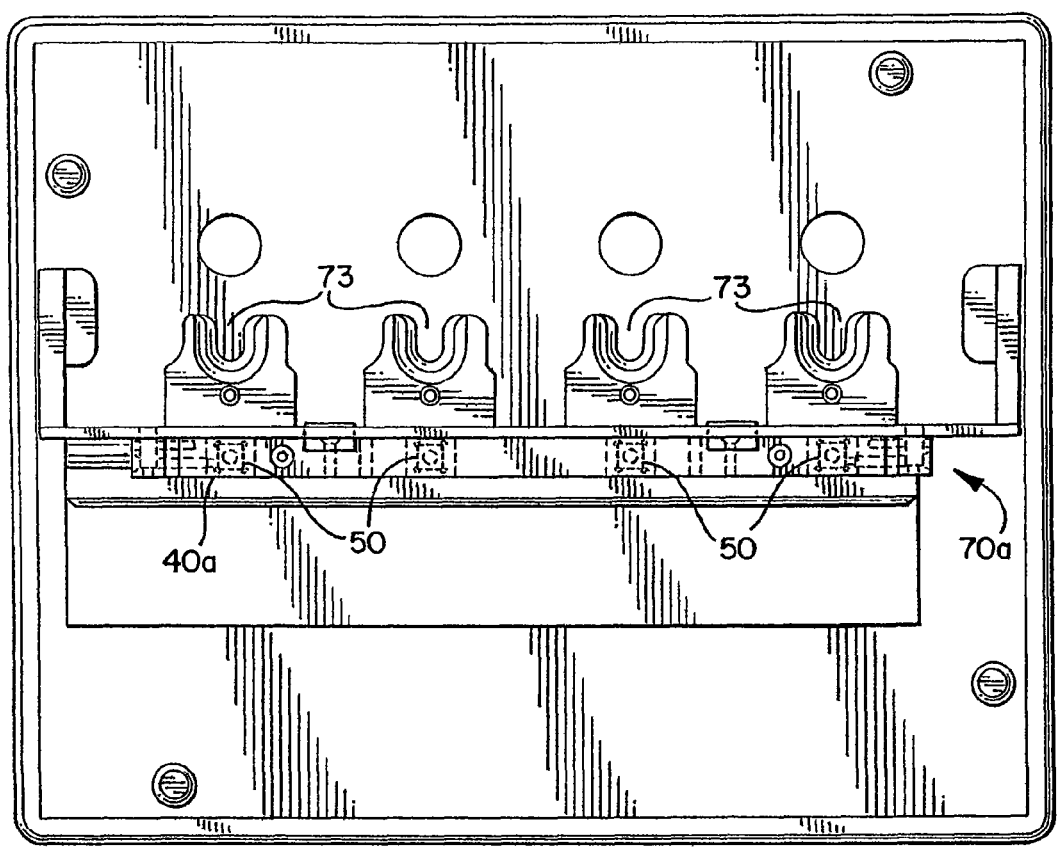
FIG. 3 is a top view showing one embodiment of a multi-site dosimeter holder attached to the bag sterilization pallet of FIG. 1.
Figure 4:
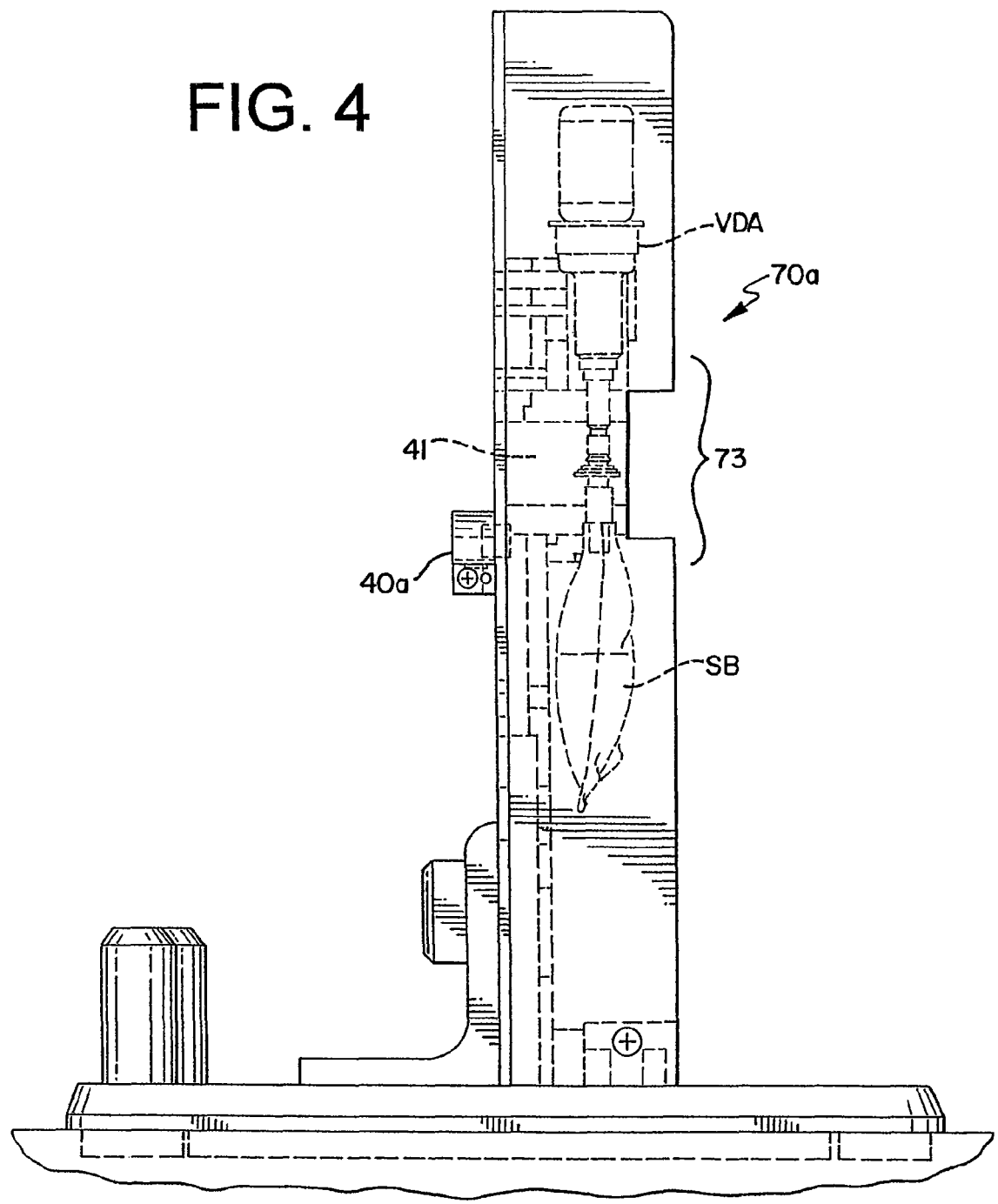
FIG. 4 is a side elevated view of one embodiment of a dosimeter holder attached to the bag sterilization pallet of FIG. 1, including a medical solution bag and vial/device shown.
Figure 5:
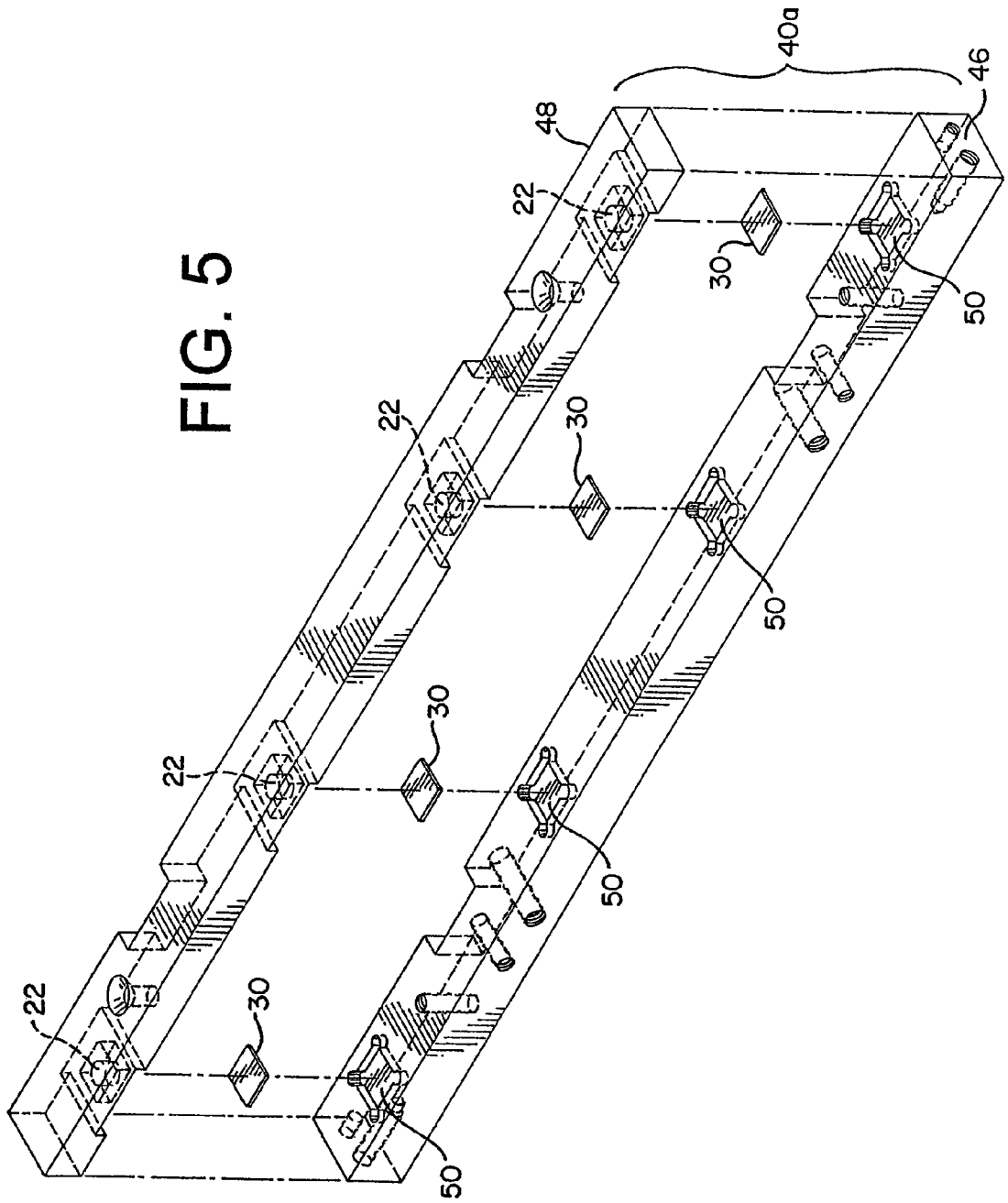
FIG. 5 is an exploded view of one embodiment of a multi-site dosimeter holder of the present invention.
Figure 9:
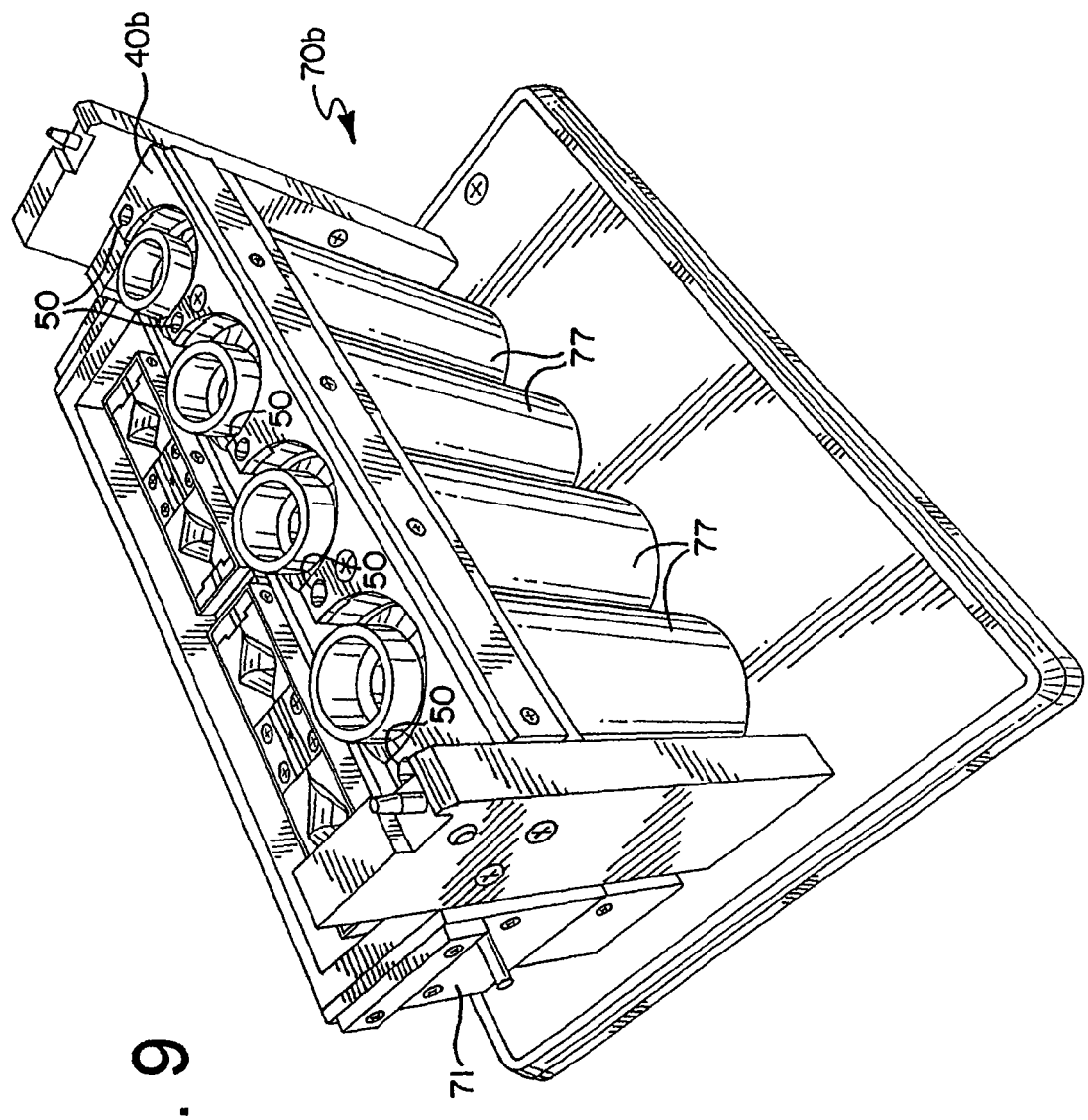
FIG. 9 is a perspective view of one embodiment of a vial/device pallet having attached thereto another embodiment of a multi-site dosimeter holder of the present invention.
Figure 10:
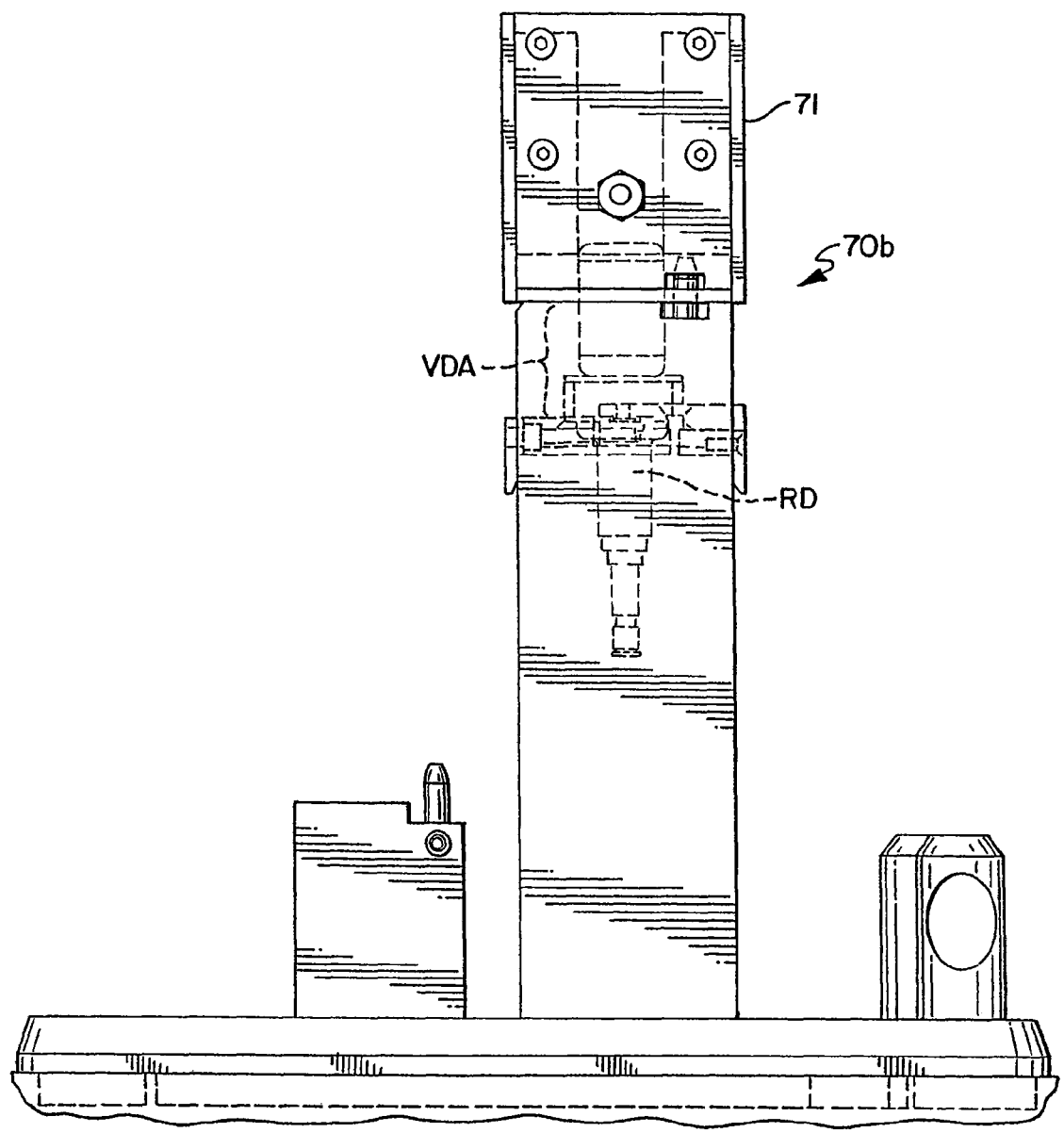
FIG. 10 is a side elevation view showing an embodiment of a multi-site dosimeter holder attached to the vial/device pallet of FIG. 9, including a device and drug vial shown connected.
Figure 11:
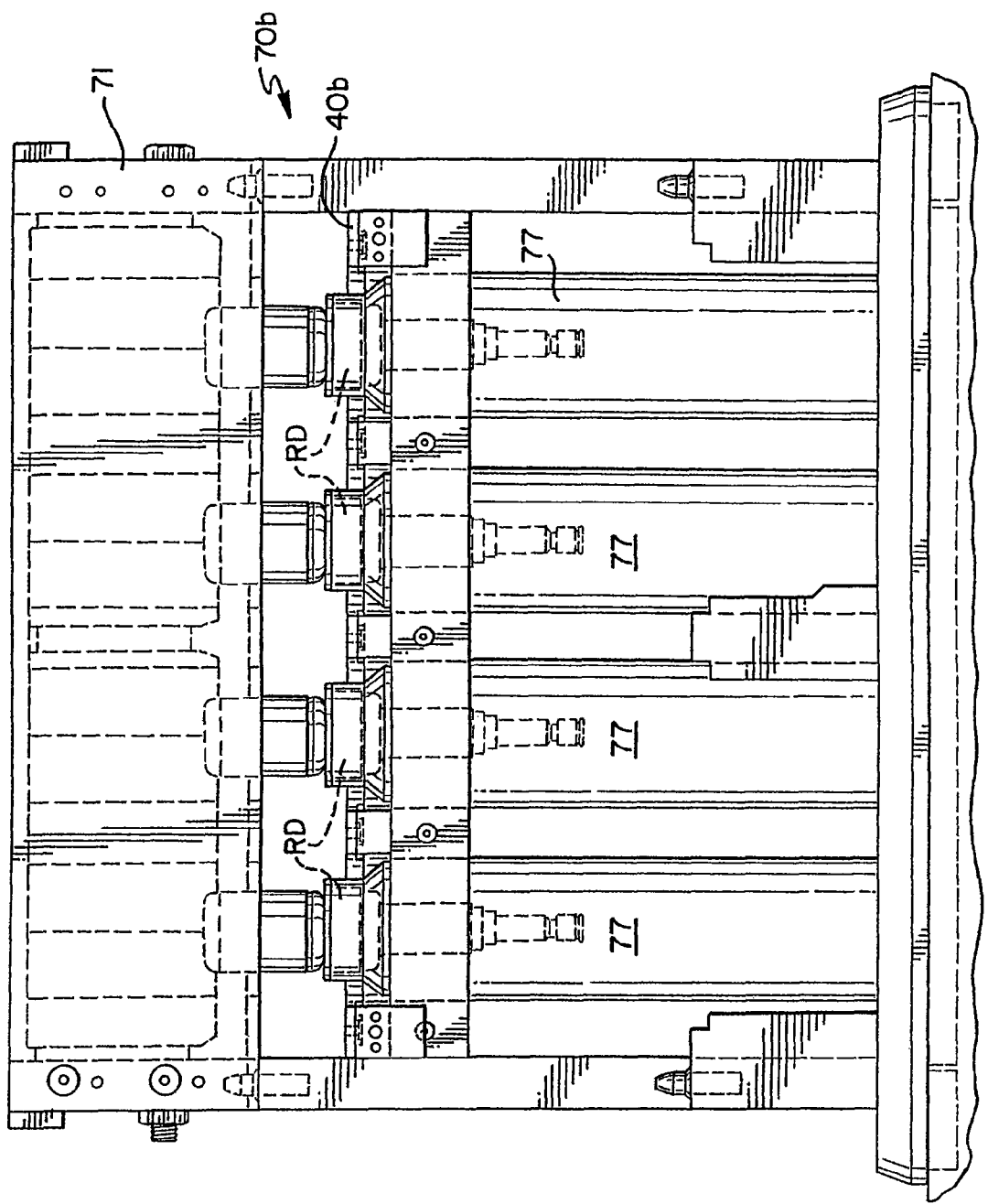
FIG. 11 is a front view showing one embodiment of a multi-site dosimeter holder attached to the vial/device pallet of FIG. 9.
Figure 12:
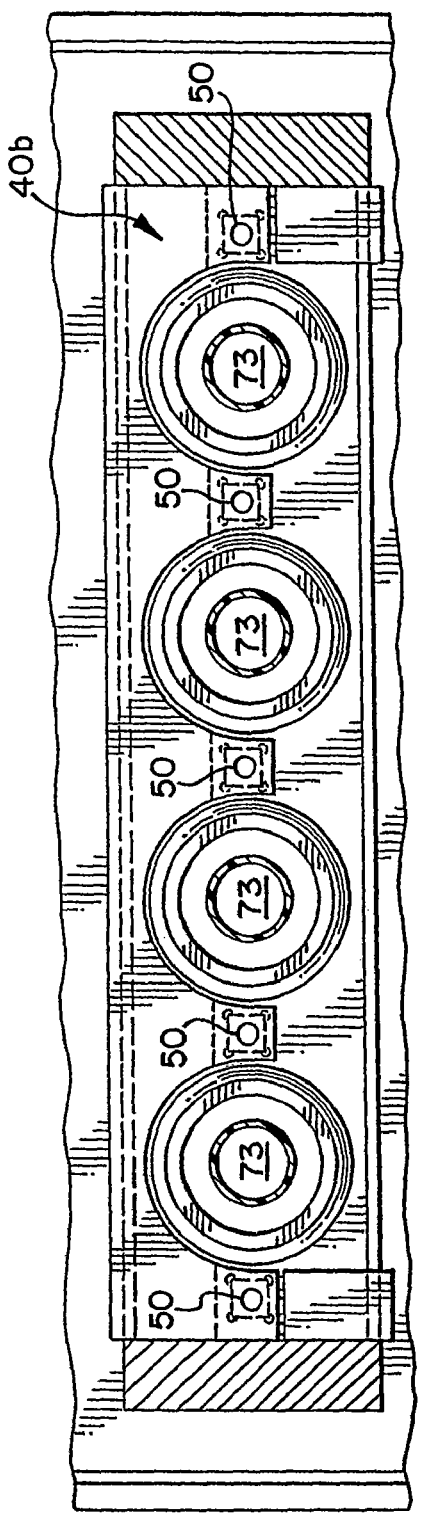
FIG. 12 is a top plan view of one embodiment of a multi-site dosimeter holder attached to the vial/device pallet of FIG. 9.

In the present invention, the bag pallet 70a is generally designed to grip and retain, via grippers 75, the tubing of as many as four medical solution bags (SB) and four vial/device assemblies (VDA) (see FIG. 4), as illustrated in FIG. 1. In this position the open end of the tubing of each medical solution bag (SB) would be aligned with an end of one of the vial/device assemblies (VDA). While these components are pre-sterilized, it is desired to make the connection between the tubing end and the vial/device in a manner that maintains the sterility. Referring to FIGS. 3 and 4, the position on the pallet 70a where the component resides is called the component site 73. Specifically, the position of the component end (the portion of the component to be connected) determines the component site 73. In the present embodiment, the ends of the two components to be connected together are maintained in such close proximity to one another that only a single component site 73 exists for each component pair. However, alternate configurations are possible.

Referring generally to the vial and device pallet of FIGS. 9-12, four cartridges 77 are shown configured to carry reconstitution devices (RD), while the vial holder 71 is shown to be configured to contain four inverted drug vials. It is similarly desirable to create a sterile connection between these components to create four complete vial/device assemblies (VDA) for later use in connecting to a sterile medical solution bag. Additional pallet designs may be contemplated for carrying other medical components for sterilization.

Returning to FIGS. 1-4, each pallet is designed to expose the retained components to the active sterile field created by the low-energy electron beam. Bag pallet 70a permits the sterilizing electron beam to pass through a window 41. Typically, as in the present invention, where more than a single e-beam tube is used to address shadowing, or where a particular component or component contents may be especially susceptible to degradation from electron beam exposure, additional separate shielding (not shown) may be provided in the sterilization booth for the exposed portions of, for example, the bag (SB) and vial/device assembly (VDA). Ideally, only the connecting ends of the components (i.e., the portions within component sites 73) are to be exposed to the electron beam field. The remaining portion of the components is preferably shielded by either the pallet or an alternative means within the sterilization booth.

In the present embodiment, while the component site 73 is exposed to the beam field, the component ends are then connected together through the actuation of at least one of the components toward the other component. Movement of the components should be limited to the constraints of the electron-beam field until a proper connection is completed.

A key aspect of the present invention is the ability to initially validate sterilization of exposed components at a specific dose level. It is a further feature of the invention to provide routine dose monitoring of the sterilization process.

The use of routine radiation monitoring devices such as dosimeters for processing have been used for many years and are widely recognized and understood in the industry. However, all of the routine monitoring dosimeter fixtures and processes used are based on the premise that the radiation source penetrates the dosimeter, its packaging, and in many cases, a fixture. This premise is based on the fact that such radiation sterilization applications involve the use of penetrating radioisotopes or high energy electrons. Due to the deep-penetrating ability of this matter, precise placement of dosimeters is not as critical nor is the direct exposure from the radiation source to the dosimeter.

The present embodiment of the invention, however, utilizes "non-penetrating" (in a relative sense) low-energy electrons. A monitoring fixture has been designed to work in the low-energy process where direct exposure of the dosimeter is necessary. In one preferred embodiment of the invention, the dosimeter is a radiochromic film. In addition to exposing the radiochromic film directly to the electron beam, the monitoring fixture is placed such that the dose to which the dosimeter film is exposed will be approximately relative to the dose the product receives. The dosimeter placement is referred to as the indicator site.

Figure 14:
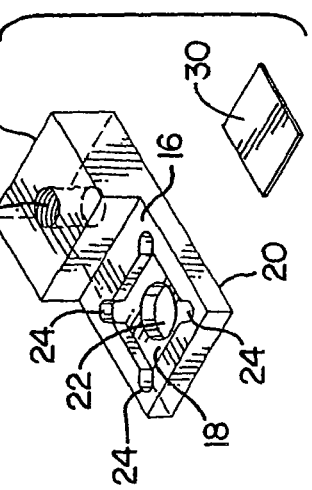
FIG. 14 is a perspective view of one embodiment of a first or upper block of a single-site dosimeter holder.
Figure 13:
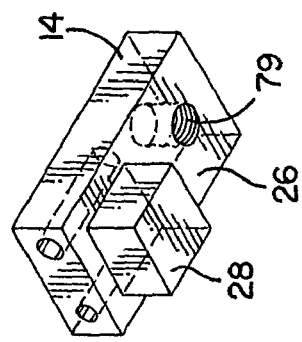
FIG. 13 is a perspective view of one embodiment of a second or lower block of a single-site dosimeter holder.
Figure 15:
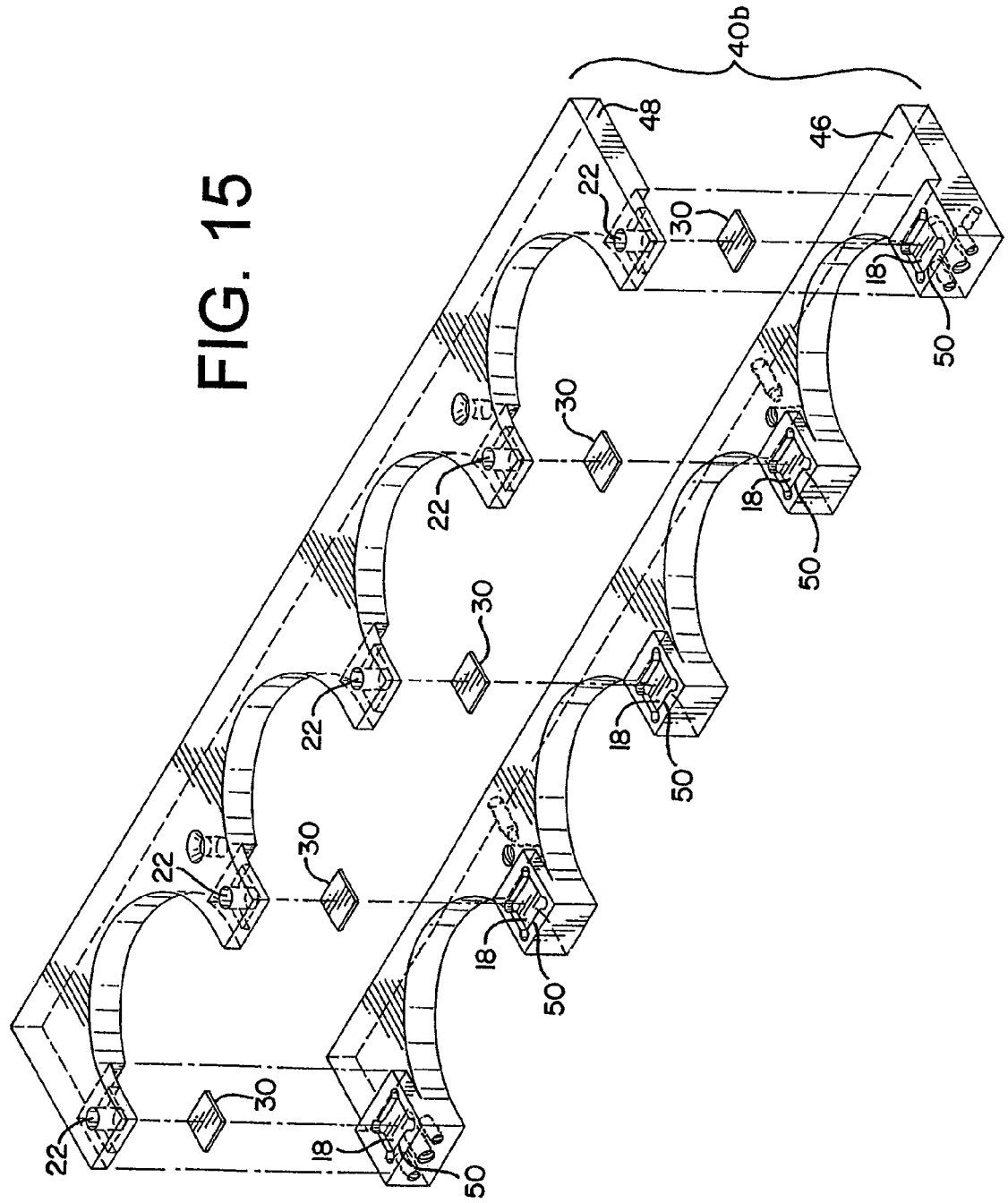
FIG. 15 is an exploded view of another embodiment of a multi-site dosimeter holder for use on the device side of the vial/device pallet of FIG. 9.
Figure 16:
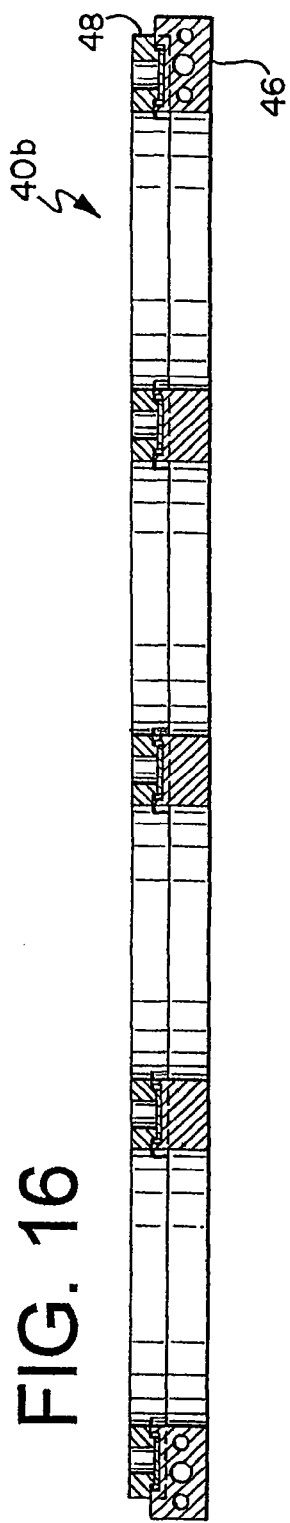
FIG. 16 is a cross-section of a multi-site dosimeter holder for attachment to the vial/device pallet shown in FIG. 9.
Figure 17:
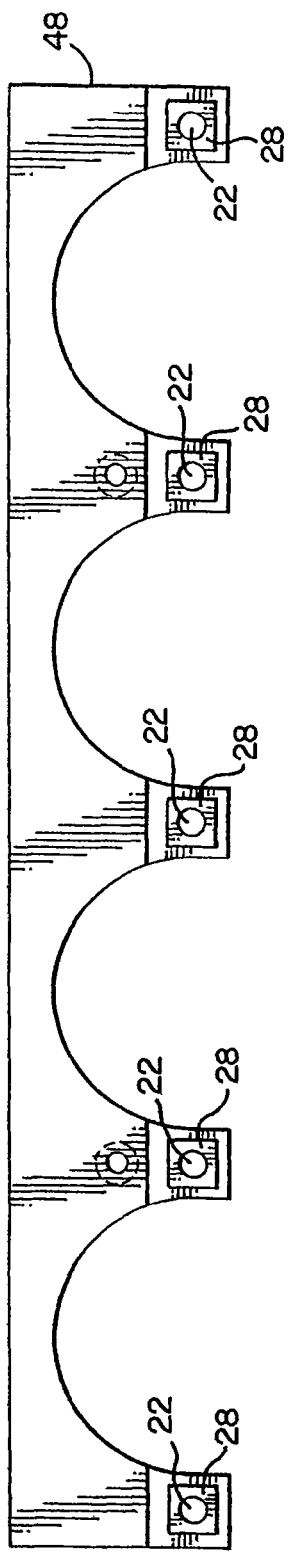
FIG. 17 is a top view of one embodiment of a second or upper block of a multi-site dosimeter holder of the present invention.
Figure 18:
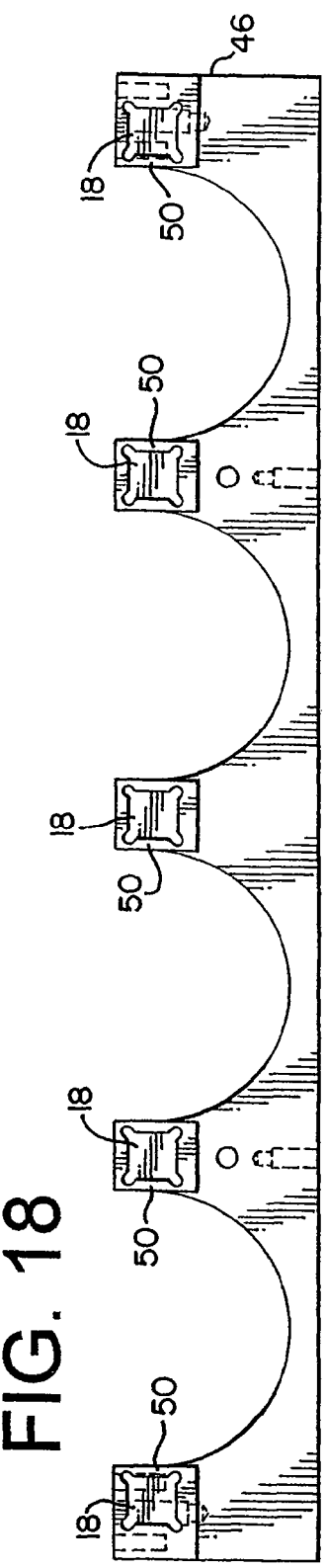
FIG. 18 is a top view of one embodiment of a first or lower block of a multi-site dosimeter holder of the present invention.
Figure 19A:
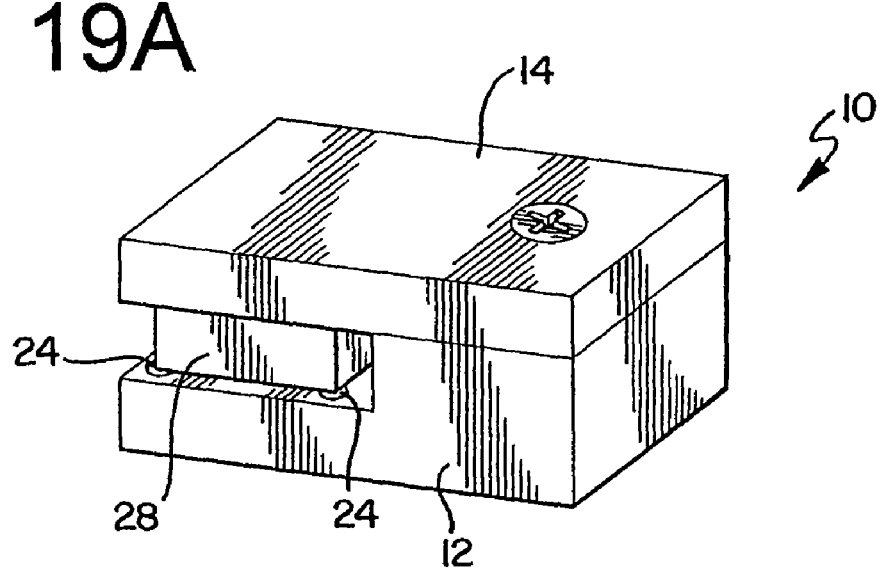
FIGS. 19(a) and 19(b) are perspective views (underside and topside, respectively) of the assembled single-site dosimeter holder shown in FIGS. 13 and 14.
Figure 19B:
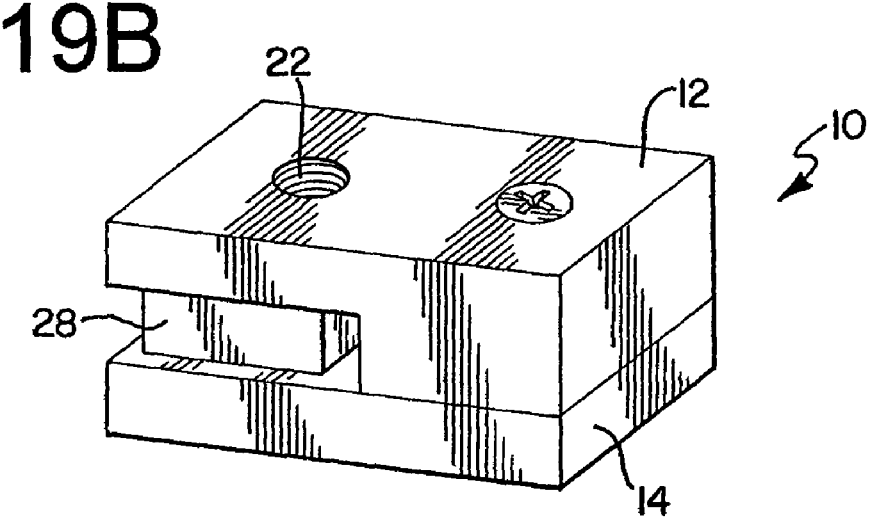

Three different sterilization validation and routine monitoring dosimeter fixtures are shown in the appended drawing figures. FIGS. 13 and 14 illustrate different halves of a basic single-site dosimeter holder 10, while the assembled fixture is shown in FIGS. 19(a) and 19(b). FIGS. 5-8 illustrate a multi-site dosimeter holder 40(a) for attachment to the bag pallet 70a of FIGS. 1-4. FIGS. 15-18 illustrate a multi-site dosimeter holder 40(b) for attachment to the vial and device pallet 70b of FIGS. 9-12. Generally speaking, the respective dosimeter holder or fixtures shown are each comprised of a basic plate configured to be attached to a pallet—either a bag pallet or vial/device pallet. The plate can be a single metal plate or devised of any number of connectable parts. It may house as few as a single dosimeter, such as a dosimeter film, or a plurality of such devices for a particular holder.

Referring to FIGS. 13, 14 and 19, halves of the single-site dosimeter holder 10 are shown. The holder 10 (when assembled) is comprised of a first dosimeter block 12 (FIG. 14) and a second dosimeter block 14 (FIG. 13). The first block 12 comprises an interior surface 16 with a substantially square cavity 18 defined therein, and an outer surface 20 with a cylindrical passage 22 to the cavity 18 passing therethrough. The cavity 18 may be of any desired shape to accommodate a radiochromic film dosimeter, which typically comes as a small square piece—though other shapes and sizes may be more suitable for alternative embodiments. The embodiment of FIG. 14 also illustrates four radiused corner notches 24 extending from the cavity 18. These notches 24 facilitate the removal of the radiochromic film dosimeter from the cavity 18. The passage 22 may also be machined to various shapes, if desired. In alternative embodiments, the passage 22 may be in the second dosimeter block 14 or pass through an adjacent side of the dosimeter block.

In the present embodiment, the second dosimeter block 14 of FIG. 13 comprises an interior surface 26 with a protrusion 28 configured to abut an interior surface of the cavity 18 of block 12. In use, a radiochromic film dosimeter 30 is positioned within the cavity 18 of the first block 12 and held in place by the protrusion 28 of the second block 14.

A first mechanism (not shown), such as a pin, bolt, or similar device, is used to pass through aperture 79 to affix the first dosimeter block 12 to the second dosimeter block 14 to form a dosimeter holder or assembly 10 (FIG. 19). Additionally, a second mechanism (not shown) may be used to affix the holder 10 to a radiation sterilization site, such as a component pallet. The first mechanism may perform the operation of the second mechanism for certain applications.

The material used for manufacturing the dosimeter holder 10 must be radiation resistant and be of sufficient density and thickness to shield the contained dosimeter 30 from indirect exposure to the electron beam. Overexposure of the dosimeter 30 is a concern as it will negatively affect validation and routine monitoring.

As a means for controlling exposure of the dosimeter 30, the size of the diameter and depth of the passage 22 may be adjusted. The larger the diameter of the passage 22 and the shorter the depth of the passage 22 (i.e., the thickness of the block material) the greater the dose the dosimeter 30 will receive. Conversely, the smaller the diameter and the longer the depth of the passage 22, the lower the dose received by the dosimeter 30. In a preferred embodiment, the passage depth is machined to 0.124 inch (3.15 mm) and the diameter is 0.234 inch (5.94 mm). The passage depth preferably falls within the range of from about 0.070 to about 0.175 inch (1.78-4.45 mm), while the preferred diameter is within the range of from about 0.175 to about 0.290 inch (4.45-7.37 mm). However, with varied applications and positioning of the assembly 10, as well as varied dosimeter thicknesses and surface areas, there exists an infinite combination of diameters and depths of the passage 22 which may be used without departing from the intended purpose of the present invention.

Referring now to FIGS. 5-8, an embodiment of a multi-site dosimeter holder 40a for the bag pallet may be more readily seen and understood. Like the single-site assembly, the multi-site holder is comprised of a first block 46 and a second block 48. The illustrated embodiment is designed with four dosimeter sites 50 equally spaced along the length of the holder 40a. The number of dosimeter sites 50 may vary with the number of component sites 73 (see FIGS. 3 and 4) provided for in the component pallet 70, though an exact one-to-one correlation is not necessary. A greater number of dosimeter sites 50 per component sites 73 (e.g., 2:1, 4:1, etc.) may improve (or be necessary for) validation and routine monitoring.

In the present embodiment, the first block 46 of the multi-site holder 40a differs from that of the single-site holder 10 in other ways. A cavity 18 for containing a radiochromic film dosimeter 30 is present, but there is no passage to the cavity in the first block 46. Rather, the second block 48, while comprising a protrusion 28 to fit within the cavity 18 of the first block 46 and retain the dosimeter therein, has a passage 22 through the protrusion 28. The function and the range of dimensions of the passage diameter and depth are otherwise identical to those of the passage 22 in the single-site dosimeter holder 10. Of course, alternative embodiments may include the passage 22 on the first block 46 requiring only different positioning of the holder 40a on the pallet 70a.

As shown in the cross-section of FIG. 6, the first and second blocks, 46 and 48, are secured together to form a multi-site holder 40a. The holder 40a is then affixed to the bag pallet 70a, as illustrated in FIGS. 1-4. In the present embodiment, the holder 40a is affixed to the backside 72 of the pallet 70a. As explained in greater detail infra, each dosimeter site 50 of the holder 40a is positioned to correspond to a component site 73 (FIG. 2) on the frontside 74 of the pallet 70a. Again, more than one dosimeter site may be used to correspond to a single component site, or vice versa. Similarly, more than one holder 40a may be employed on each pallet 70a—for example, one on the frontside and one on the backside of the pallet, or one for the first component and one for a second component held on the pallet.

Referring to FIGS. 15-18, another embodiment for a multi-site dosimeter holder, holder 40b is illustrated. This holder 40b has a 5:4 dosimeter site 50 to component site 73 ratio. While the holder 40b is shaped notably different than the bag pallet dosimeter holder 40a of FIGS. 5-8, the dosimeter sites 50 between the two embodiments are actually identically configured. The alternative embodiments disclosed for holder 40a also may be utilized for holder 40b.

FIGS. 9-12 illustrate the attachment of the holder 40b to the vial/device pallet 70b in a position which places the dosimeter sites 50 proximate the component sites 73. Each component site 73 is sandwiched between two dosimeter sites 50 for improved validation.

Having discussed embodiments of the physical details of the present invention, the following is a detailed discussion of the validation process and a sterilization system in which the referenced holders as well as preferred operational parameters may be implemented.

One of the first steps in the validation process is to determine the sterilization dose to product required to achieve the desired SAL. One of two approaches is taken in selecting the sterilization dose: selection of sterilization dose using either bioburden information or information obtained by incremental dosing; or using a sterilization does of 25 kGy following substantiation of the appropriateness of the dose. Once established, the minimum radiation dose can be achieved in several ways known by those skilled in the art, including increasing the intensity (current) of the electron beam or by increasing the time that the product is in the electron beam field.

The next step is to determine the dose distribution of the product being sterilized. The dose distribution study or dose mapping is performed to identify the zones of minimum and maximum dose within the product(s) processed and to assess the reproducibility of the process. This information is then used to select the routine monitoring position for routine processing. That is, a location for the routine monitoring dosimeter must be determined such that during sterilization the level of radiation absorbed by the dosimeter (which is readily measurable) is proportional to that of the component to be sterilized (which is not readily measurable).

With a low energy electron beam, the correlation between the dose received by the product and the dose received by the dosimeter is difficult to achieve because of complex product geometries and the tendency of the dosimeter to be saturated in the direct path of the electron field. With the present invention, a correlation between the measured radiation exposure of the dosimeter and the desired dose to product can be made.

Figure 20A:
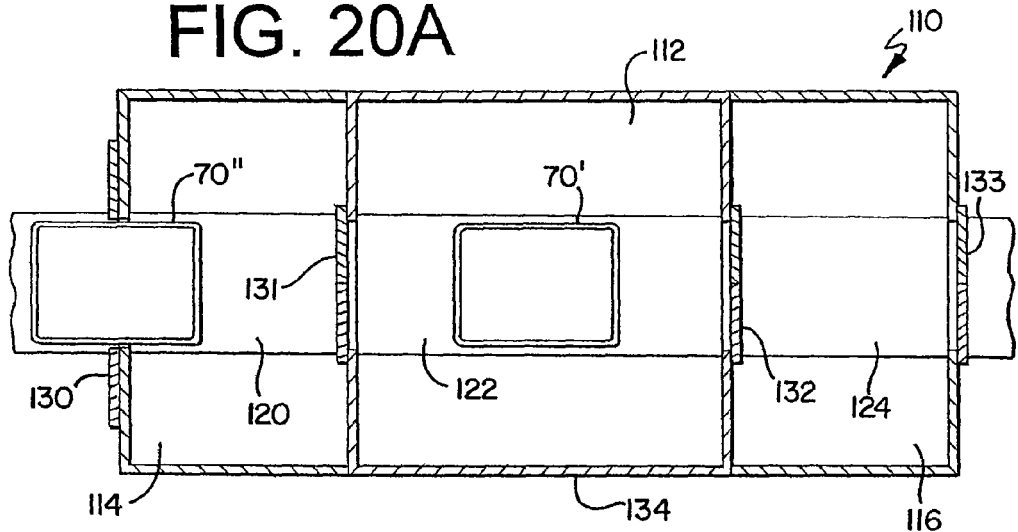
FIGS. 20A-C are schematics of a sterilization booth illustrating the sequencing of chamber door openings to move pallets through the sterilization process.
Figure 20B:
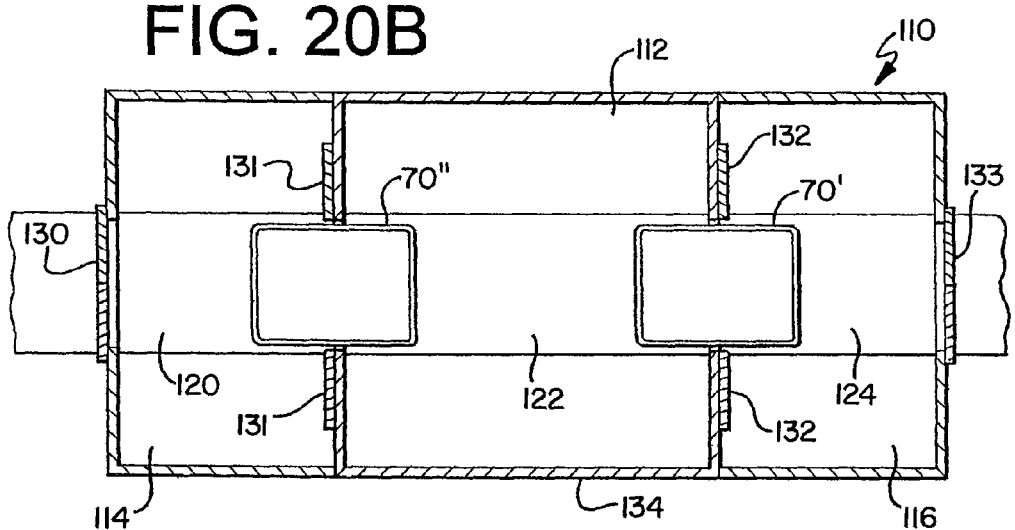
Figure 20C:
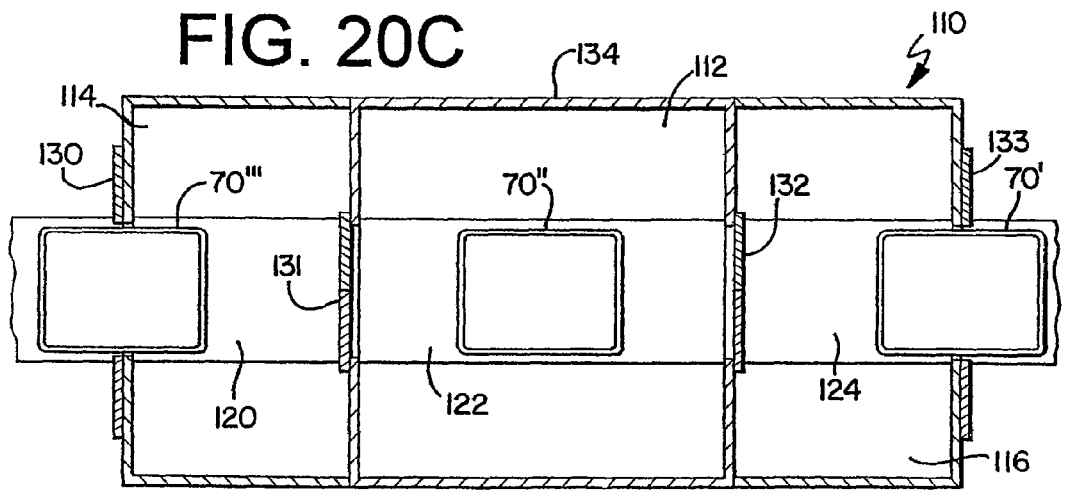
Figure 21:
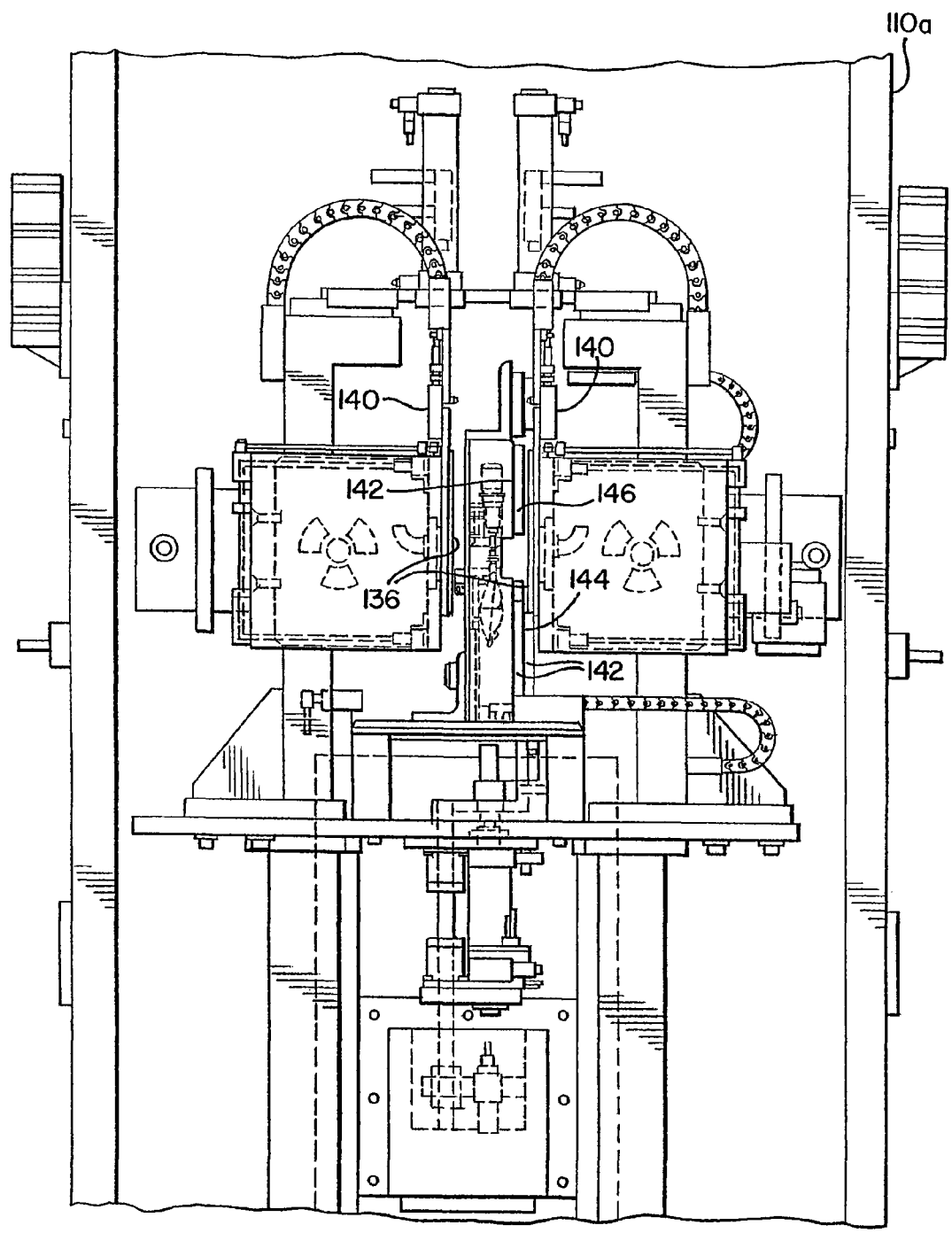
FIGS. 21 and 22 are cut away views of the internal components of the bag sterilization chamber; and, FIG. 23 is a cut away side view of a vial/device sterilization booth.
Figure 22:
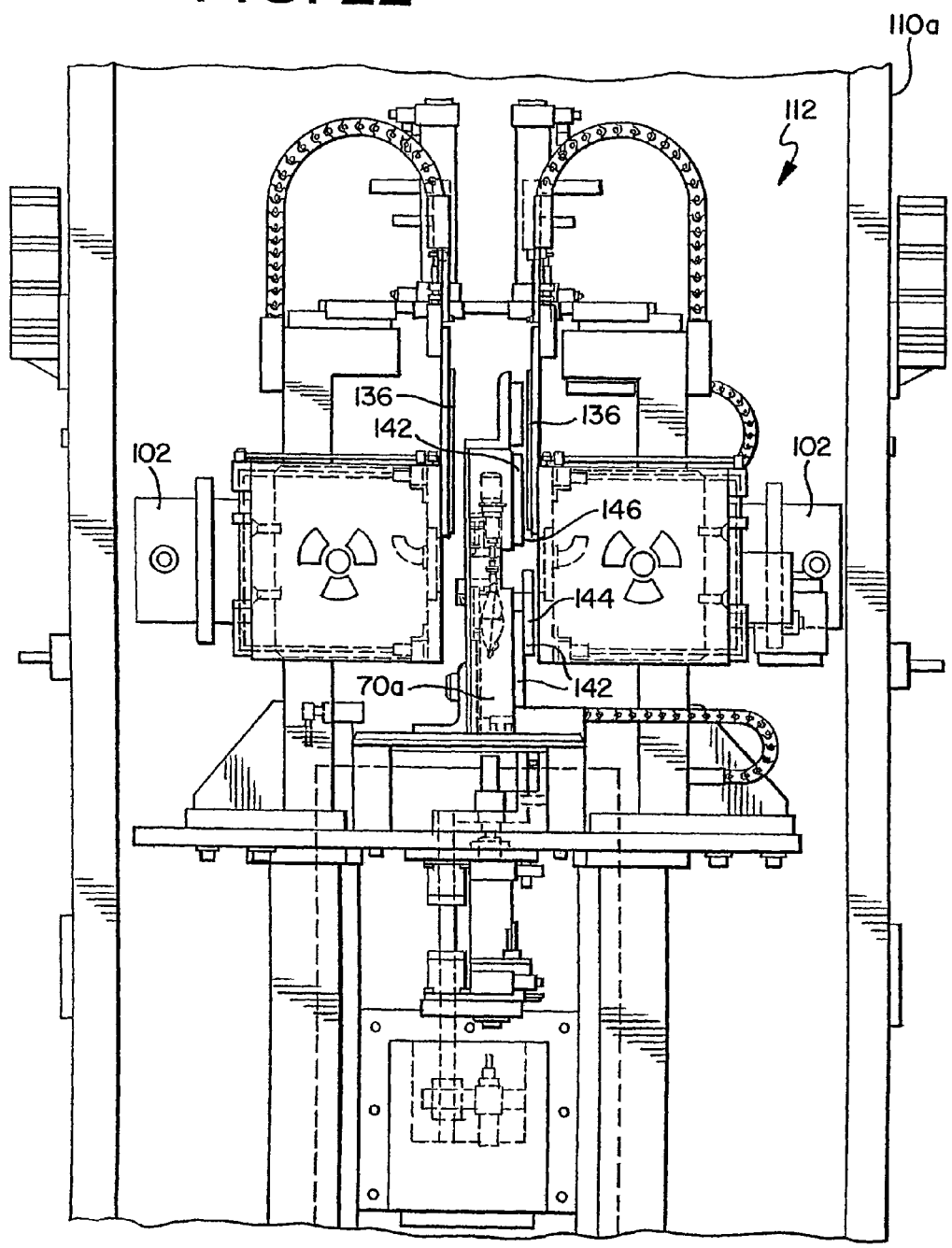

Referring to FIGS. 20-22, a preferred embodiment of the system for sterile connecting a plurality of components comprises a sterilization chamber 112 having a low-energy electron beam source 102, and a component pallet 70 capable of positioning at least two components within a sterilizing cloud created by the low-energy e-beam source within the sterilization chamber 112. A transportation source (not shown), such as a conveyor belt or indexing table, may be used to convey the component pallet 70 from a staging area to the sterilization chamber 112.

Figure 23:
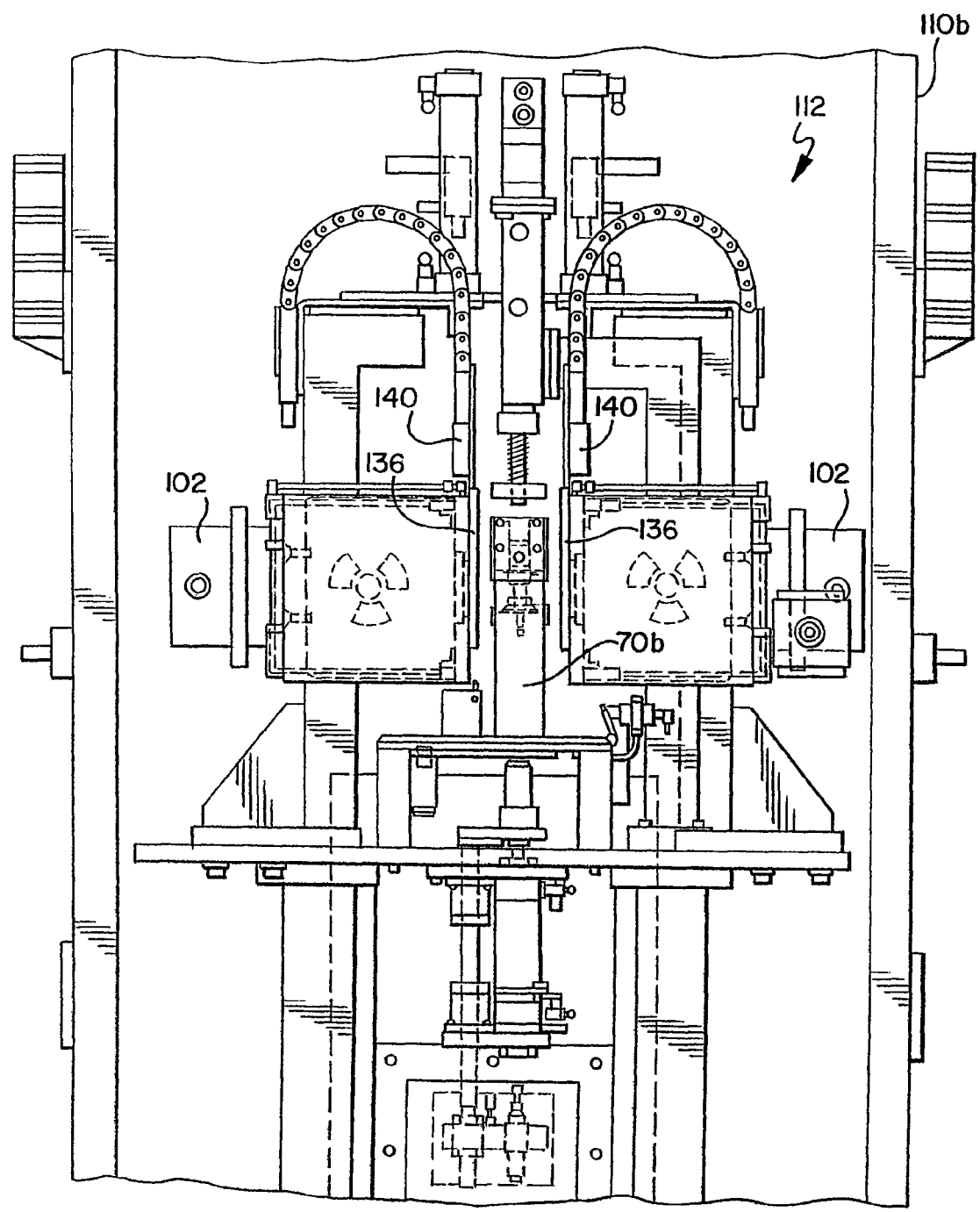

In the embodiment of FIG. 20, the sterilization chamber 112 is preferably situated as a center compartment within a larger sterilization booth 110. The preferred sterilization system is comprised of two booths: a bag sterilization booth 110a (FIG. 21) and a vial/device sterilization booth 110b (FIG. 23). The two booths, 110a and 110b, are identical in purpose, so the following discussion will merely refer to bag sterilization booth 110a. However, where key differences exist between the booths, such differences will be noted in this text and the appended drawing figures.

The two booths 110a and 110b are divided into three chambers: a pre-sterilization chamber 114, the sterilization chamber 112, and a post-sterilization chamber 116. Each chamber is comprised of a set of entrance doors and a set of exit doors. The exit doors 131 for the pre-sterilization chamber 114 also act as the entrance doors for the sterilization chamber 112. Likewise, the sterilization chamber exit doors 132 also function as the post-sterilization chamber 116 entrance doors. The doors are preferably laterally sliding doors actuated by, for example, a hydraulic mechanism reacting to a sensor (not shown) and control system (not shown). As space allows, the doors may be designed to slide vertically or horizontally. A single panel or bi-parting panels may be used as well. These added features and their implementation would be well-understood by those skilled in the relevant art of automated system design.

The four sets of chamber doors 130, 131, 132, and 133, are comprised of a one-inch lead core with a quarter-inch stainless steel exterior lining. Similarly, the chamber walls 134 are built to prevent accidental exposure of external personnel to radiation created by the electron beam source. Use of higher energy sources may require additional shielding. The sterilization chamber 112 should also be comprised of an appropriate ventilation means due to the creation of ozone from these energy sources.

As shown in FIGS. 21 and 22, the e-beam source is preferably provided by two oppositely positioned low-energy electron beam tubes 102. Presently, there only are a small number of suppliers for such tubes. Tube and beam dimension and output operating parameters are only a few factors which may guide selection. The preferred e-beam tubes for the present embodiment are approximately ten-inches in width and two-inches in height, and operate in the range of 60 to 125 KeV. Other suitable electron beam tubes may exist and those skilled in the art would understand what modification would be necessary to implement such tubes into the present system.

By training the resulting electron clouds of the opposing e-beam tubes 102 at the position of the pallet window 41 of either the bag pallet 70a or the vial/device pallet 70b, an electron "flood area" is created where connection of the components is contemplated. Connection within the flood area insures that sterilization is maintained at every corner, crevice, and surface of the components. That is, shadowing caused by juxtapositioned surfaces is minimized, if not eliminated.

While the use of two electron beam sources is preferred for the present embodiment, it is contemplated that a single electron beam could be used in some applications. For example, the components could be rotated within the resulting electron cloud to effect sterilization, or the source beam could revolve about the components for the same effect. Additionally, any number of electron beams may be used in an array fashion to further address shadowing of very complicated connections or oddly shaped components.

Referring now to FIG. 20A-C, the movement of pallets 70 through the three chambered booth 110 can be more readily understood. Beginning with a completely empty booth 110, the door 130 into the pre-sterilization chamber 114 is opened. Here the first component pallet 70' is held until the door 130 is again closed. Then, after door 131 is opened and the first component pallet 70' enters the sterilization chamber 112, the door 131 is completely closed, and door 130 is opened to permit the entrance of a second component pallet 70", as shown in FIG. 20A. At this time, the first component pallet 70' is subject to sterilization, the details of which will be explained in greater detail below. The door 130 is then closed as before, while door 132 is opened to allow the movement of the first component pallet 70' to the post-sterilization chamber 116. Simultaneously, door 131 is opened to allow the second component pallet 70" to enter the sterilization chamber 112, as shown in FIG. 20B. Doors 131 and 132 are then closed. At this point, as shown in FIG. 20C, the first component pallet 70' is in the post-sterilization chamber 116, acting as a holding chamber, and the second component pallet 70" is in the sterilization chamber 112.

Still referring to FIG. 20C, doors 130 and 133 open to allow the movement of a third component pallet 70'" into the pre-sterilization chamber 114 and the first component pallet 70' out of the post-sterilization chamber 116. Doors 130 and 133 then close. The booth 110 would then contain second component pallet 70" in the sterilization chamber 112 and the third component pallet 70'" in the pre-sterilization chamber 114. The sequence is then repeated from the opening of doors 130 and 133 until all component pallets have passed through all three chambers of the booth 110. Following such a progression maintains a sealed door on either side of the electron source at all times, thereby providing a full-time barrier against the escape of stray radiation from the sterilization chamber. Naturally, other sequences may be devised to achieve this important safety precaution.

Movement of the pallets is controlled by the three independent conveyor surfaces 120, 122, and 124. The first conveyor surface 120 is responsible for receiving a pallet from the system and transporting the pallet into the pre-sterilization chamber 114. The first conveyor surface 120 and a second conveyor surface 122 work together to transport the pallet into the sterilization chamber 112. After sterilization, the second conveyor surface 122 and a third conveyor surface 124 cooperate to position the pallet within the post-sterilization chamber 116. Finally, the third conveyor surface 124 transports the pallet to the system for resumed handling. With alternate indexing through the chambers, variations on the number of conveyor surfaces used may be made. Those skilled in the art would understand how to correlate the indexing of pallets to the movement of the conveyor surfaces should variations be necessary.

Within the sterilization chamber 112, referring to FIGS. 21-23, the bag pallet 70a (FIG. 21) or the vial/device pallet 70b (FIG. 23) is positioned between the two electron beam sources 102. At this time, as shown in FIG. 21, the shutters 136 are in a closed position. The shutters 136 are liquid cooled steel panels used to block the electron beam window before and after component sterilization and connection. As with the chamber doors, it is necessary that the shutters 136 be dense enough to provide proper shielding, so any cooling elements (which may require hollowing of the panel) are preferably absent from a central portion of the shutter 136 where direct incidence of the electron beam is realized.

Referring to FIGS. 21 and 22, the shutters 136 are attached to a pneumatic actuator 140 which is responsive to a controller (not shown). A single controller may be used to control the chamber doors, 130, 131, 132, and 133, the conveyor surfaces 120, 122, and 124, and the shutters 136, if desired. After the chamber doors 131 and 132 are in a closed position (FIG. 20A), the appropriate controller can activate pneumatic actuator 140 to raise shutters 136 (FIG. 22). At this point, component exposure is controlled by the position of the components within the resulting electron cloud (preferably within the electron flood area) as well as the time of exposure (i.e., the time the shutters are raised).

Unlike the vial/device pallet 70b, the bag pallet 70a has additional heat shielding to protect the product of the components from electron beam exposure. Referring to FIGS. 21 and 22, a liquid-cooled, double-paneled heat shield 142 is initially positioned within the sterilization chamber 112. The lower portion 144 of the heat shield 142 is used to shield the bag component, and the upper portion 146 to shield the vial/device component 70b. As the bag holding portion of the bag pallet 70a is raised by actuator 140 to raise the bag component in the connecting step of the sterilization process, the lower portion 144 of the heat shield 142 moves simultaneously to maintain the shielding of the bag component. Upon snap connection of the two components together, the lower portion 144 abuts the upper portion 146 of the heat shield 142. The heat shield 142 is retracted (ie., the lower portion 144 is returned to its starting position) only after the shutters 136 are closed and then simultaneously with the return of the actuated bag holding portion of the bag pallet 70a.

Referring to FIG. 20C, the pallet 70 is then transferred to the post-sterilization chamber 116 for holding, as described above. From the post-sterilization chamber 116, the pallet 70 is capable of travel to other stations for further processing.

In a preferred embodiment, a pre-selected percentage of the sterilized pallets (e.g., 10%, 30%, 50%, etc.) may be routed to a verification station (not shown). At the verification station, the dosimeter holder, 40a and 40b, may be removed from the pallet, 70a and 70b, respectively. The holder may then be disassembled to gain access to the dosimeters 30. Of course, the dosimeters 30 should be handled with the necessary tools (e.g., tweezers) to prevent contamination.

After removal from the dosimeter holder 40, the absorbed radiation of each dosimeter 30 can be measured. If the measured radiation dose level is at or above the necessary level for achieving the required or desired SAL for each dosimeter, then the respective pallet may be validated as "sterile." The ability to validate the sterility of the components is a result of the correlated relationship determined to exist between the dosimeter film and the component on the pallet.

The pallet may re-enter the assembly process. The dosimeter holder 40 can now be fitted with new dosimeters and reattached to a suitable pallet 70 to repeat the process.

While the invention has been shown and described with reference to the preferred embodiments, it will be understood by those skilled in the art that various changes in form and detail may be made therein without departing from the spirit and scope of the invention as defined by the appended claims.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

We claim:
1. A radiation sterilization verification device comprising:
   a dosimeter;
   a first dosimeter block including an interior surface with a cavity defined therein, wherein the dosimeter is positioned within the cavity;
   a second dosimeter block configured to operate with the first dosimeter block, the second dosimeter block including an interior surface forming a protrusion configured to abut an interior surface of the cavity of the first dosimeter block, at least one of the first and second dosimeter blocks having a radiation resistant material and a sufficient density and thickness to shield the dosimeter from indirect exposure to radiation.
2. The device of claim 1, further comprising:
   a mechanism to affix the first dosimeter block to the second dosimeter block.

3. The device of claim 1, further comprising a mechanism to affix the first dosimeter block to a radiation sterilization site.

4. The device of claim 1, further comprising a mechanism to affix the first dosimeter block and the second dosimeter block to a radiation sterilization site.

5. The device of claim 4, wherein the mechanism to affix the first dosimeter block to the second dosimeter block includes the mechanism to affix the first dosimeter block and the second dosimeter block to the radiation sterilization site.

6. The device of claim 2, wherein the mechanism to affix the first the first dosimeter block to the second dosimeter block includes friction.

7. The device of claim 1, wherein the first dosimeter block includes a single cavity.

8. The device of claim 1, wherein the first dosimeter block includes a plurality of cavities, and wherein the second dosimeter block has a corresponding number of protrusions each configured to abut an interior surface of one of the cavities.

9. The device of claim 1, further comprising a passage defined within either the first or second dosimeter block to allow radiation to reach the cavity.

10. The device of claim 9, wherein a diameter of the passage is in the range of from about 4.45 mm (0.175 inch) to about 7.37 mm (0.290 inch).

11. The device of claim 10, wherein the diameter of the passage is about 5.94 mm (0.234 inch).

12. The device of claim 9, wherein a depth of the passage is in the range of from about 1.78 mm (0.070 inch) to about 4.45 mm (0.175 inch).

13. The device of claim 12, wherein the depth of each passage is about 3.15 mm (0.124 inch).

14. The device of claim 1, further comprising a plurality of passages defined within either the first or second dosimeter block to allow radiation to reach each cavity.

15. The device of claim 14, wherein a diameter of each passage is in the range of from about 4.45 mm (0.175 inch) to about 7.37 mm (0.290 inch).

16. The device of claim 15, wherein the diameter of each passage is about 5.94 mm (0.234 inch).

17. The device of claim 14, wherein a depth of each passage is in the range of from about 1.78 mm (0.070 inch) to about 4.45 mm (0.174 inch).

18. The device of claim 17, wherein the depth of each passage is about 3.15 mm (0.124 inch).

19. A radiation sterilization verification device comprising:
a plurality of dosimeters;
a first dosimeter block including an interior surface with a plurality of cavities defined therein, wherein one of the plurality of dosimeters is positioned within each cavity; and
a second dosimeter block configured to operate with the first dosimeter block, the second dosimeter block including an interior surface with a plurality of protrusions each configured to abut an interior surface of one of the plurality of cavities of the first dosimeter block, the first and second dosimeter blocks having a radiation resistant material and a sufficient density and thickness to shield the dosimeter from radiation.

20. The device of claim 19, further comprising:
a mechanism to affix the first dosimeter block to the second dosimeter block.

21. The device of claim 19, further comprising a mechanism to affix the first dosimeter block to a radiation sterilization site.

22. The device of claim 19, further comprising a mechanism to affix the first dosimeter block and the second dosimeter block to a radiation sterilization site.

23. The device of claim 22, wherein the mechanism to affix the first dosimeter block to the second dosimeter block includes the mechanism to affix the first dosimeter block and the second dosimeter block to a radiation sterilization site.

24. The device of claim 20, wherein the mechanism to affix the first the first dosimeter block to the second dosimeter block includes friction.

25. The device of claim 19, further comprising a passage defined within either the first or second dosimeter block to allow radiation to reach the cavity.

26. The device of claim 25, wherein a diameter of the passage is in the range of from about 4.45mm (0.174 inch) to about 7.37mm (0.290 inch).

27. The device of claim 26, wherein the diameter of the passage is about 5.94mm (0.234 inch).

28. The device of claim 25, wherein a depth of the passage is in the range of from about 1.78mm (0.070 inch) to about 4.45mm (0.175 inch).

29. The device of claim 28, wherein the depth of each passage is about 3.15mm (0.124 inch).

30. A radiation sterilization verification device comprising:
a dosimeter;
a first dosimeter block including an interior surface with a plurality of cavities defined therein, wherein the dosimeter is positioned within one of the plurality of cavities;
a second dosimeter block configured to operate with the first dosimeter block, the second dosimeter block including a plurality of protrusions, each protrusion configured to abut an interior surface of one of the plurality of cavities, at least one of the first and second dosimeter blocks having a radiation resistant material and a sufficient density and thickness to shield the dosimeter from indirect exposure to radiation.

* * * * *